United States Patent [19]

Fujiwa et al.

[11] Patent Number: 5,569,773

[45] Date of Patent: Oct. 29, 1996

[54] PROCESS FOR PRODUCING A COMPOSITION COMPRISING EPOXY COMPOUNDS HAVING HYDROXYL GROUP

[75] Inventors: Takaaki Fujiwa, Hiroshima; Tomohisa Isobe, Yamaguchi, both of Japan

[73] Assignee: Daicel Chemical Industries, Ltd., Osaka, Japan

[21] Appl. No.: 275,244

[22] Filed: Jul. 15, 1994

Related U.S. Application Data

[62] Division of Ser. No. 123,980, Sep. 21, 1993, Pat. No. 5,367,088, which is a continuation of Ser. No. 925,618, Aug. 6, 1992, abandoned, which is a division of Ser. No. 773,653, Oct. 15, 1991, Pat. No. 5,155,243.

[30] Foreign Application Priority Data

Feb. 15, 1990 [JP] Japan ..................................... 2-34511

[51] Int. Cl.$^6$ ...................... C07D 301/14; C07D 301/16; C07D 301/12; C07D 301/19

[52] U.S. Cl. .......................... 549/525; 549/526; 549/529; 549/531

[58] Field of Search ................................... 549/525, 526, 549/529, 531

[56] References Cited

U.S. PATENT DOCUMENTS

| | | |
|---|---|---|
| 2,687,406 | 8/1954 | Foster ........................................ 549/525 |
| 2,745,848 | 5/1956 | Greenspan et al. ..................... 549/525 |
| 2,786,066 | 3/1957 | Frustick et al. . | |

(List continued on next page.)

FOREIGN PATENT DOCUMENTS 2914988  10/1980  Germany .

(List continued on next page.)

OTHER PUBLICATIONS

Herbest et al., "Aspects of Stereochemistry. Part XI*. Epoxide Formation in the Cyclohexene and Bicyclo Heptene Series," Journal of the Chemical Society, pp. 221–226, Jan. 1959.

Primary Examiner—Joseph E. Evans
Attorney, Agent, or Firm—Sughrue, Mion, Zinn Macpeak & Seas

[57] ABSTRACT

The present invention provides a composition represented by the formula

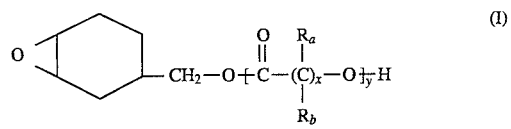

(wherein x is an integer of 3 to 7, y is an integer of 0 to 50, and $R_a$ and $R_b$ are H, methyl group, or propyl group and each of the $R_a$ and $R_b$ groups may be replaced with any of the other groups simultaneously) and useful as a raw material or modifier for resins for use in coating compositions, adhesives, epoxy resins, and the like, and further provides a process for producing a composition comprising compounds represented by the above formula (I) which process is characterized in that a compound represented by the formula

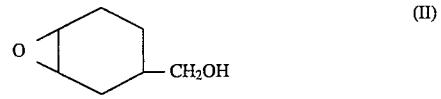

is reacted with a lactone at 30° to 20° C. or compounds represented by the formula

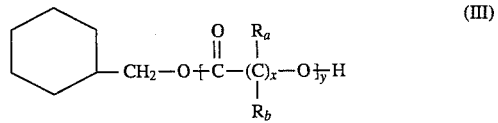

(wherein x, y, $R_a$, and $R_b$ have the meanings as defined above) are epoxidized at 0° to 80° C. using a peroxide.

6 Claims, 24 Drawing Sheets

U.S. PATENT DOCUMENTS

| | | |
|---|---|---|
| 2,794,029 | 5/1957 | Phillips et al. . |
| 2,929,827 | 3/1960 | Carruthers . |
| 3,459,736 | 8/1969 | Dalibor . |
| 4,086,294 | 4/1978 | Koleske et al. . |
| 4,159,925 | 7/1979 | Schreyer et al. .......................... 549/525 |
| 4,849,532 | 7/1989 | Boehme et al. .......................... 549/526 |

FOREIGN PATENT DOCUMENTS

| | | |
|---|---|---|
| 3838185 | 6/1989 | Germany . |
| 132877 | 6/1987 | Japan ........................ 549/525 |
| 164675 | 7/1987 | Japan ........................ 549/525 |
| 62-205071 | 9/1987 | Japan . |
| 63-225615 | 9/1988 | Japan . |
| 196177 | 4/1989 | Japan . |
| 186876 | 7/1989 | Japan ........................ 549/525 |
| 591471 | 2/1978 | U.S.S.R. . |
| 639882 | 3/1979 | U.S.S.R. . |
| 789522 | 12/1980 | U.S.S.R. ................................ 549/525 |
| 1115277 | 5/1968 | United Kingdom . |

PROCESS FOR PRODUCING A COMPOSITION COMPRISING EPOXY COMPOUNDS HAVING HYDROXYL GROUP

This is a divisional of application Ser. No. 08/123,980 filed Sep. 21, 1993, now U.S. Pat. No. 5,367,088, which is a continuation of application Ser. No. 07/925,618 filed Aug. 6, 1992, now abandoned, which is a divisional of application Ser. No. 07/773,653 filed Oct. 15, 1991, now issued as U.S. Pat. No. 5,155,243 on Oct. 13, 1992.

TECHNICAL FIELD

The present invention relates to a composition which comprises compounds having an epoxy group and a hydroxyl group and is industrially useful as a raw material or modifier for various resins for use in coating compositions, adhesives, epoxy resins, and the like, and also relates to a process for producing the composition.

BACKGROUND ART

Conventionally known as compounds having an epoxy group and hydroxyl group are glycidol and the like.

However, these compounds have poor storage stability because they are unstable in the presence of a slight amount of an acid or alkali, so that the epoxy group readily reacts with a hydroxyl group and a polymerization reaction thus proceeds, and further, side reactions are apt to take place when these compounds are subjected to various reactions.

On the other hand, as another compound having an epoxy group and hydroxyl group, the compound

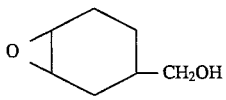
(II)

is known.

However, although stable as compared with the above-described glycidol and the like, this compound has been unsuited for use in various applications because the following intramolecular reaction takes place.

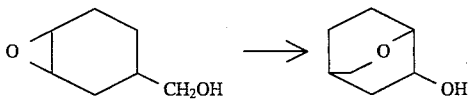

This may be because the compound becomes stable in entropy due to the formation of the 6-membered rings within the molecule.

Further, since the above compound (II) is poor in flexibility, it poses problems when used in applications such as, for example, coating compositions.

DISCLOSURE OF THE INVENTION

An object of the present invention is to provide a compound having an epoxy group and hydroxyl group and free from the above-described disadvantages.

The present inventor has conducted intensive studies in order to attain the above object and, as a result, it has been found that a compound having a specific structure is excellent in stability, ring-opening polymerization reactivity, and the property of imparting flexibility. Further, processes for efficiently producing such a compound have also been found. The present invention has thus been accomplished.

That is, the present invention is: "a composition comprising compounds having the following structure

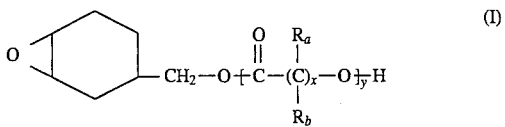
(I)

(wherein x represents an integer of 3 to 7, y represents a statistical distribution of integers of 0 to 50, $R_a$ and $R_b$ represent H, methyl group, or propyl group, and each of the groups of $R_a$ and $R_b$ may be replaced with any of the other groups simultaneously)"; and "a process for producing a composition comprising compounds having the following structural formula

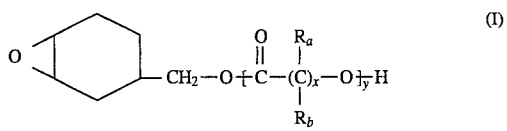
(I)

(wherein x represents an integer of 3 to 7, y represents an integer of 0 to 50, $R_a$ and $R_b$ represent H, methyl group, or propyl group, and each of the groups of $R_a$ and $R_b$ may be replaced with any of the other groups simultaneously), characterized in that a compound having the structure

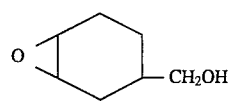
(II)

is reacted with a lactone at 30° to 200° C. in the presence of a catalyst"; and

"a process for producing a composition comprising compounds having the following structural formula

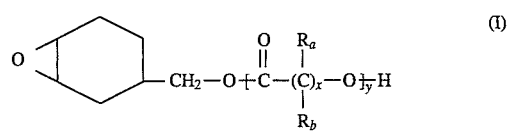
(I)

(wherein x represents an integer of 3 to 7, y represents an integer of 0 to 50, $R_a$ and $R_b$ represent H, methyl group, or propyl group, and each of the groups of $R_a$ and $R_b$ may be replaced with any of the other groups simultaneously), characterized in that a composition comprising compounds having the following structure

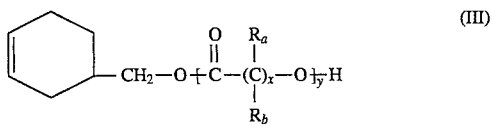
(III)

is epoxidized at 0° to 80° C. using a peroxide".

The composition of this invention which comprises epoxy compounds (I) having a hydroxyl group can be produced by either of the following two processes.

That is, these are a process in which compound (II) is reacted with a lactone in the presence of a catalyst (hereinafter referred to as Route A)

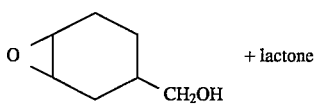

↓

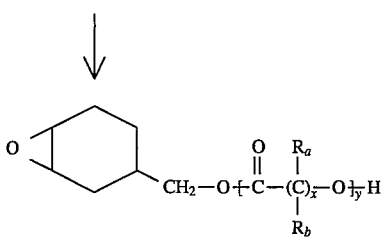

and a process in which a composition comprising compounds (III) is reacted with an epoxidizing agent (hereinafter referred to as Route B).

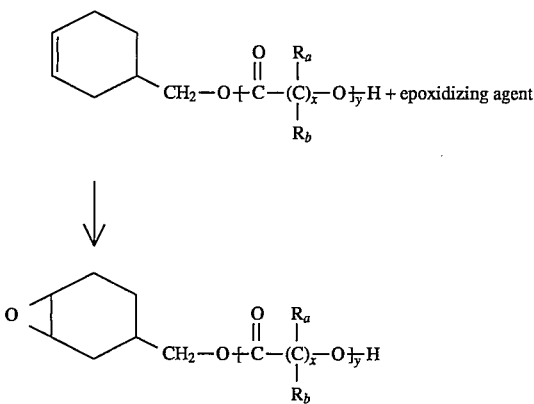

In the process of Route A, compound (II) as a raw material can be obtained by epoxidizing 3-cyclohexene 1-methanol with an epoxidizing agent.

Examples of the above epoxidizing agent include organic percarboxylic acids such as performic acid, peracetic acid, perpropionic acid, perbenzoic acid, m-chloroperbenzoic acid, and the like, peracetic acid produced from hydrogen peroxide and acetic acid, acetic anhydride, or sulfuric acid, and the like.

Examples of the lactone include ε-caprolactone, trimethylcaprolactone, β-methyl 67 -valerolactone, and butyrolactone.

The composition comprising compounds (I) can be obtained by reacting those in the presence of a catalyst.

As this catalyst, use may be made of a titanium compound such as tetrabutoxy titanate, tetrapropoxy titanate, tetraethoxy titanate, or the like, an organotin compound such as tin octylate, dibutyltin oxide, dibutyltin laurate, or the like, a tin halide such as stannous chloride, stannous bromide, stannous iodide, or the like, or a heteropoly-acid such as phosphotungstic acid, silicotungstic acid, or the like.

The reaction may be conducted at a temperature of 30° to 230° C.

In the case of using a titanium- or tin-based catalyst, the temperature desirably is from 100° C. to 180° C.

This is because if the reaction temperature is 100° C. or lower, the amount of the catalyst used is increased and this produces an adverse influence when the compound (II) is further reacted with an isocyanate and with a urethane resin and, further, there are cases where the increased catalyst amount causes the coating composition to suffer discoloration.

On the other hand, if the reaction temperature is 180° C. or higher, there is the possibility that the epoxy in compound (II) might undergo ring opening or the lactone that has undergone addition might be depolymerized.

In the case of using phosphotungstic acid or the like, on the other hand, the reaction may be allowed to proceed at a lower temperature of 30° to 100° C. The amount of the catalyst used is from 0.01 ppm to 2,000 ppm of the starting materials.

It is desirable that the catalyst be used in a smaller amount because there is the possibility that the catalyst might adversely affect as described above.

However, if the catalyst amount is 0.01 ppm or less, much time is required for completing the reaction even at an elevated temperature and, hence, such a process is uneconomical.

The molar amount of the lactone reacted is desirably from 1 to 15 times that of compound (II).

This is because if the molar amount of the addition-reacted molar amount exceeds 15 times, use of the thus-obtained compounds as a coating composition results in coating films which are too soft.

In the case where 2 mol of ε-caprolactone is allowed to undergo addition to 1 mol of compound (II), the reaction product is a composition which comprises compounds represented by formula (I) and in which the unreacted compound of y=0 and adducts of y=1, 2, 3, . . . are distributed statistically, since the rate of the ring- opening reaction of the lactone with the hydroxyl group of compound (II) does not differ so much from the rate of the ring-opening reaction of the lactone with the lactone terminal of the product.

However, there is no need of separating these, and the mixture may be used as it is in various applications such as synthesis of a urethane resin etc.

It is also unnecessary that the lactone used be reacted completely to 0%, and the reaction mixture can be used, as it is, as a raw material for syntheses, although it may be used after the unreacted lactone is evaporated.

For example, the product obtained by reacting compound (II) with ε-caprolactone at 140° C. using tetrabutoxytitanium (hereinafter TBT) as a catalyst is a composition containing the following.

| ε-Caprolactone | 0.8% |
|---|---|
| Compound (II) | 0.6% |
| Compounds (I) | 89.6% |
| TBT | 0.0010% |

By reacting this composition as it is with an isocyanate compound, a urethane compound can be obtained.

If required, the reaction may be carried out using a solvent which is of the aromatic or aliphatic hydrocarbon, ester, ether, amide, or amine type.

The thus-obtained solution (dope) of the composition comprising compounds (I) in the solvent used can be handled as it is as a commodity.

It is desirable that the above reaction be conducted so as to yield a less colored product.

Accordingly, better results are obtained when the reaction is effected under $N_2$ to avoid oxidation by oxygen.

On the other hand, the composition comprising compounds (I) has a molecular weight distribution, which generally is apt to be wide if the reaction has been conducted at a high temperature for a long time period.

Further, when an Sn-based catalyst and a Ti-based catalyst are compared, use of a Ti-based catalyst is prone to result in a wider distribution.

In order to obtain a product having a narrow molecular weight distribution, a low temperature and low-concentration use of an Sn-based catalyst are preferred.

Further, in order to obtain one with a wide molecular weight distribution, a high temperature and use of a Ti-based catalyst are desirable.

According to applications, the molecular weight distribution of the composition to be produced can be made either narrow or wide.

The composition comprising compounds (I) may also be synthesized by the copolymerization of two or more kinds of lactones.

For example, a composition comprising (I) which is copolymers obtained from a mixture of ε-caprolactone and β-methyl δ-valerolactone or of ε-caprolactone and trimethylcaprolactone can be obtained.

Although the composition comprising compounds (I) which has been produced by this process and is in a crude liquid form after the reaction may be used as it is, it contains the catalyst. This catalyst may cause runaway or inhibition of reactions or discoloration, according to applications.

For this reason, a chelating agent or the like may be added to this crude liquid to mask the catalyst.

For example, masking of the catalyst can be attained by adding 2-ethylhexyl acid phosphate in a molar amount 1 to 100 times that of the catalyst.

According to the process of Route B, on the other hand, the composition comprising compounds (I) can be obtained by allowing a lactone to undergo addition to 3-cyclohexene 1-methanol and epoxidizing the resulting adduct with an epoxidizing agent.

The composition comprising compounds (III) is obtained by allowing a lactone to undergo addition to 3-cyclohexene 1-methanol in the presence of a catalyst.

3-Cyclohexene 1-methanol to be used as a raw material can be obtained by the hydrogenation reaction of tetrahydrobenzaldehyde.

As the catalyst for the lactone addition, use may be made of a titanium compound such as tetrabutoxy titanate, tetrapropoxy titanate, tetraethoxy titanate, or the like, an organotin compound such as tin octylate, dibutyltin oxide, dibutyltin laurate, or the like, a tin halide such as stannous chloride, stannous bromide, stannous iodide, or the like, or a heteropoly-acid such as phosphotungstic acid, silicotungstic acid, or the like.

The reaction may be conducted at a temperature of 30° to 230° C.

In the case of using a titanium- or tin-based catalyst, the temperature desirably is from 100° to 180° C.

If the temperature is 100° C. or lower, the amount of the catalyst used is increased and this adversely affects the subsequent epoxidization reaction etc.

On the other hand, if the temperature is 230° C. or higher, there is the possibility that the lactone that has undergone addition might be depolymerized.

In the case of using phosphotungstic acid or the like, on the other hand, the reaction may be allowed to proceed at a lower temperature of 30° to 100° C. The amount of the catalyst used is from 0.01 ppm to 2,000 ppm.

It is desirable that the catalyst be used at a lower concentration because there is the possibility that the catalyst might adversely affect as described above.

However, if the catalyst amount is 0.01 ppm or less, much time is required for completing the reaction even at an elevated temperature and, hence, such a process is uneconomical.

The amount of the lactone reacted is desirably from 1 to 15 mol per mol of tetrahydrobenzyl alcohol (hereinafter referred to as THBA).

This is because if the addition-reacted molar amount exceeds 15, coating compositions to be prepared by using an epoxidized product are too soft.

In the case where 2 mol of ε-caprolactone is allowed to undergo addition to mol of THBA, the reaction product is a composition which comprises compounds represented by formula (III) and in which the unreacted compound of y=0 and adducts of y=1, 2, 3 ... are distributed statistically, since the rate of the ring-opening reaction of the lactone with the hydroxyl group of the THBA does not differ so much from the rate of the ring-opening reaction of the lactone with the lactone terminal of the product.

However, there is no need of separating these, and the mixture may be used as it is in the subsequent epoxidization step. It is also unnecessary that the lactone used in the reaction be made completely 0%, and the reaction mixture can be used, as it is, as a raw material for syntheses, although it may be used after the unreacted lactone is evaporated.

For example, the composition comprising compounds (III) is a product which is obtained by reacting ε-caprolactone at 160° C. using tetrabutoxytitanium (TBT) as a catalyst and which is a composition containing the following.

| ε-Caprolactone | 0.2% |
| (III) | 96.2% |
| THBA | 3.6% |
| TBT | 0.0010% |

By reacting this composition as it is with an epoxidizing agent, a product can be obtained.

It is desirable that the above reaction be conducted so as to yield a less colored product.

Accordingly, better results are obtained when the reaction is effected under $N_2$ to avoid oxidation by oxygen.

Since the composition comprising the thus-yielded compounds (III) has a relatively high viscosity, it is desirable that a solvent be added in order to uniformly disperse the epoxidizing agent to be added in the reaction system. As the solvent, an aromatic compound, ether, aliphatic hydrocarbon, ester, or the like may be used in the case of peracetic acid.

Examples of epoxidizing agents that can be used include peracids and hydroperoxides.

Examples of the peracids include performic acid, peracetic acid, perbenzoic acid, trifluoroperacetic acid, and the like.

Of these, peracetic acid is the preferred epoxidizing agent since it is being industrially produced in large quantities, is available at low cost, and has good stability.

Examples of the hydroperoxides include hydrogen peroxide, tert-butyl hydroperoxide, cumene peroxide, and the like.

In conducting the epoxidization reaction, whether a solvent is used or not is determined and the reaction temperature is regulated, according to the apparatus and the properties of the raw materials.

The range of usable reaction temperatures is determined by the reactivity of the epoxidizing agent used.

In the case of peracetic acid which is the preferred epoxidizing agent, 0° to 70° C. is preferred.

At 0° C. or lower, the reaction is slow, while at 70° C., decomposition of the peracetic acid takes place.

Further, in the case of combined use of tert-butyl hydroperoxide, which is an example of hydroperoxides, and molybdenumdioxide diacetylacetonate, 20° C. to 150° C. is preferred for the same reason.

The molar ratio of an introduced epoxidizing agent to unsaturated bonds may be varied according to purposes such as how many unsaturated bonds are to be allowed to remain.

In the case where compounds having a large proportion of epoxy groups are desired, it is preferred to add an epoxidizing agent in an amount equimolar with unsaturated groups or in a larger amount.

However, it is usually disadvantageous to exceed two times in mol from the standpoints of economy and the problem of side reactions as described next. In the case of peracetic acid, its amount preferably is 1 to 1.5 times in mol.

Since there are cases where peracids decompose to generate oxygen in the presence of a slight amount of metal ions, it is desirable to add a stabilizer to the reaction system.

For example, it is phosphoric acid, phosphoric acid-potassium, phosphoric acid-sodium, sodium ammonium hydrogenphosphate, pyrophosphoric acid, potassium pyrophosphate, sodium pyrophosphate, potassium 2-ethylhexylpyrophosphate, sodium 2-ethylhexyltripolyphosphate, potassium 2-ethylhexyltripolyphosphate, sodium 2-ethylhexyltetrapolyphosphate, or potassium 2-ethylhexyltetrapolyphosphate. The incorporated amount is from 1 ppm to 1,000 ppm in the crude reaction liquid.

After completion of the reaction, the solvent is removed from the crude liquid and the residue can be a product as it is.

However, since discoloration may occur, a less colored product can be obtained by adding water before the solvent is removed, washing the crude reaction liquid, and then removing the solvent etc.

For example, in the case where peracetic acid was used as epoxidizing agent and ethyl acetate was used as solvent, water may be added in an amount almost equivolume with the crude reaction liquid.

After washing, the resulting mixture is allowed to separate, subsequently the aqueous layer as the lower layer is removed and the upper layer is taken out, and then the solvents are removed to obtain the desired product as the residue.

It is desirable to further repeat the water-washing once or twice.

This is for removing slight amounts of impurities which will be coloring ingredients.

With respect to conditions for the removal of low-boiling ingredients by distillation, it can be attained by heating to the boiling point of the solvent at ordinary pressure.

However, since it is desirable that the heating temperature be as low as possible because the decomposition etc. of the product itself are accelerated, it is preferred to conduct it under a reduced pressure.

The reaction is carried out continuously or batch-wise, and in the case of continuous reaction, either of a complete mixing type and a piston flow type is possible.

For the industrial removal of low-boiling ingredients, a thin film-type evaporator can be used.

In the case where the product has been synthesized by the B Route process, there are cases where since low-molecular compounds are dissolved in the aqueous layer by water-washing, the product remaining in the organic layer contains a reduced amount of low-molecular compounds.

This, however, does never practically adversely affect the final product.

BEST MODES FOR CARRYING OUT THE INVENTION

The present invention is explained below by means of examples.

EXAMPLE 1 (Synthesis Route A)

Into a flask equipped with a nitrogen-introducing tube, thermometer, and stirring device were introduced 251.7 g of compound (II), 448.3 g of ε-caprolactone [2 mol of ε-caprolactone per mol of compound (II)], and 0.014 g of TBT. Reaction was then conducted at 130° C. for 6 hours, while nitrogen gas was kept being blown in.

The product was analyzed and, as a result, the oxirane oxygen was found to be 3.58%, viscosity 137 cps/45° C., residual ε-caprolactone 0.82%, and acid value 1.1 KOHmg/g.

Figure 1:
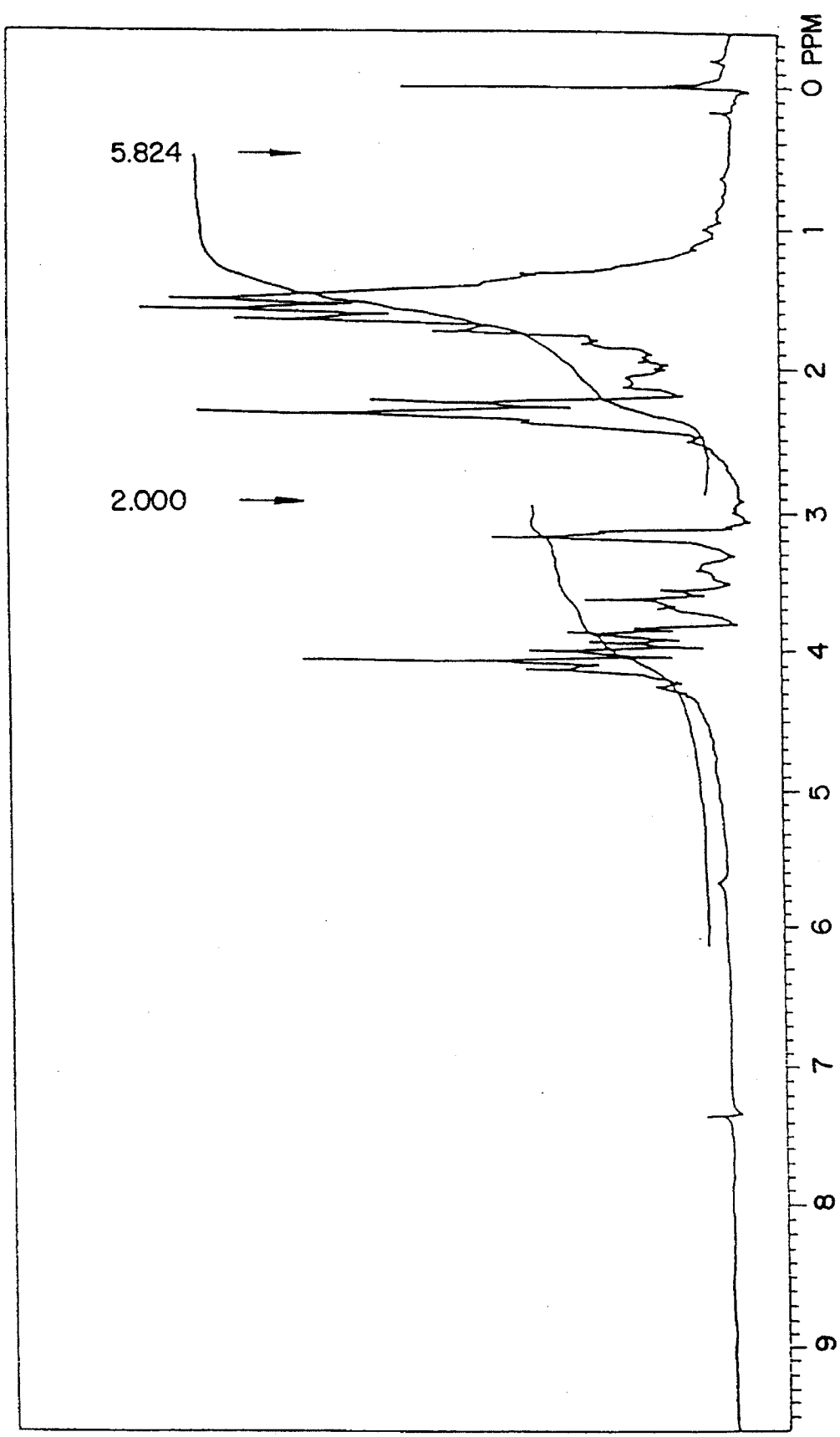
FIG. 1 is an NMR spectral chart for the product obtained in Example 1.
Figure 2:
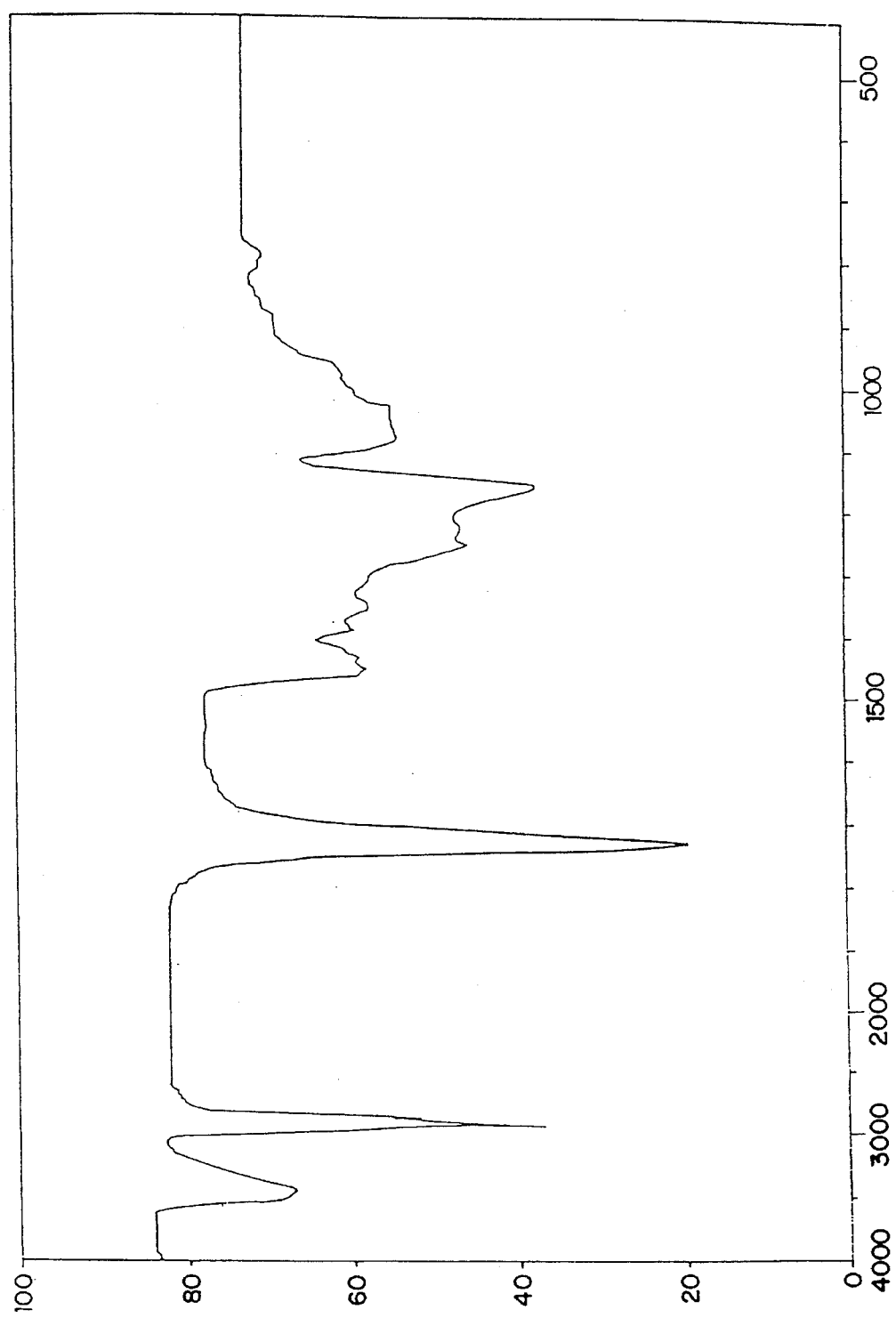
FIG. 2 is an infrared absorption spectral chart for the same.

Further, the NMR spectrum (FIG. 1) and infrared absorption spectrum (FIG. 2) of the product were measured. As a result, these spectra indicated the structure of compounds (I) which had been formed by the ring-opening polymerization of 2 mol, on the average, of ε-caprolactone with the hydroxyl group of compound (II).

Figure 3:
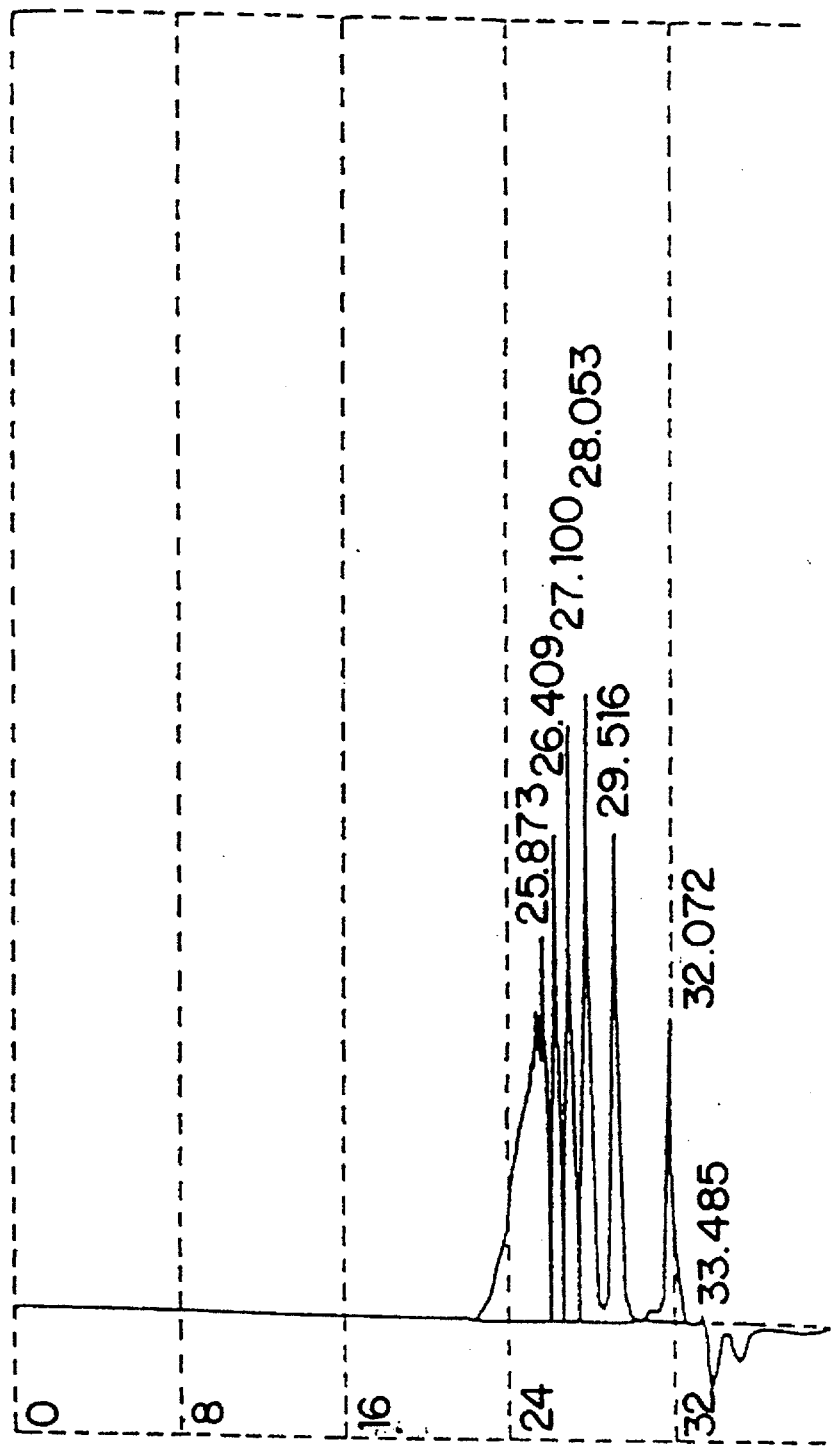
FIG. 3 is a chart obtained in a molecular weight distribution measurement of the same.

Molecular weight distribution was further measured and, as a result, the chart as shown in (FIG. 3) was obtained.

From the ratio between peak areas, this reaction product was found to be a mixture of compounds (I) which had the following distribution in terms of the number of addition-reacted ε-caprolactone introduced in the structural formula of compound (I).

| | |
|---|---|
| y = 0: | 9.58% |
| y = 1: | 13.52% |
| y = 2: | 16.13% |
| y = 3: | 15.07% |
| y = 4: | 11.77% |
| y = 5 or more: | 33.7% |

EXAMPLE 2 (Synthesis Route A)

Into the same apparatus as that in Example 1 were introduced 64.0 g of compound (II), 171.9 g [3 mol per mol of compound (II)] of ε-caprolactone, and 0.0048 g of TBT. Reaction was then conducted at 120° C. for 6 hours, while nitrogen gas was kept being blown in.

The product was analyzed and, as a result, the oxirane oxygen was found to be 3.06%, viscosity 179 cps/45° C., residual ε-caprolactone 0.5%, and acid value 1.1 KOHmg/g.

Figure 4:
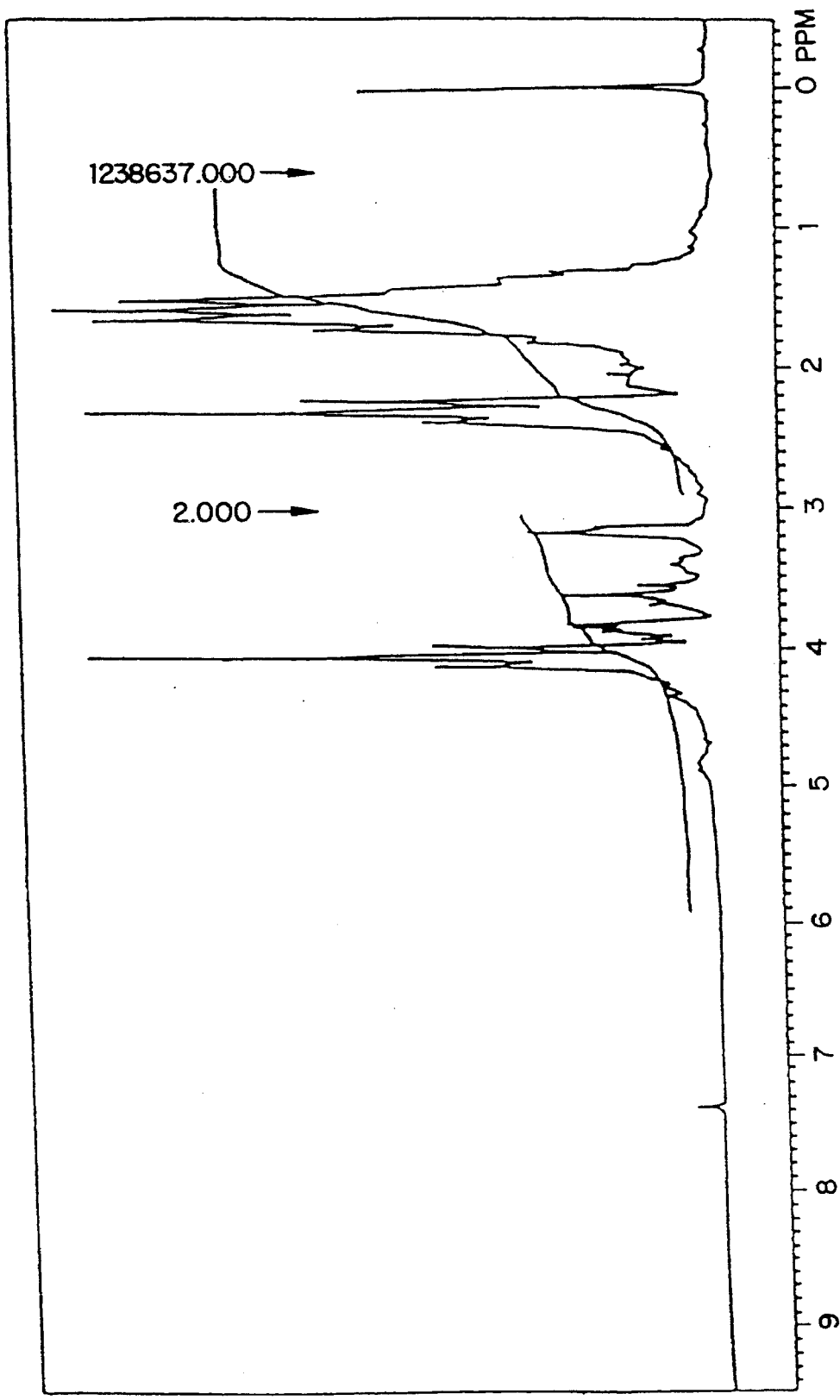
FIG. 4 is an NMR spectral chart for the product obtained in Example 2.
Figure 5:
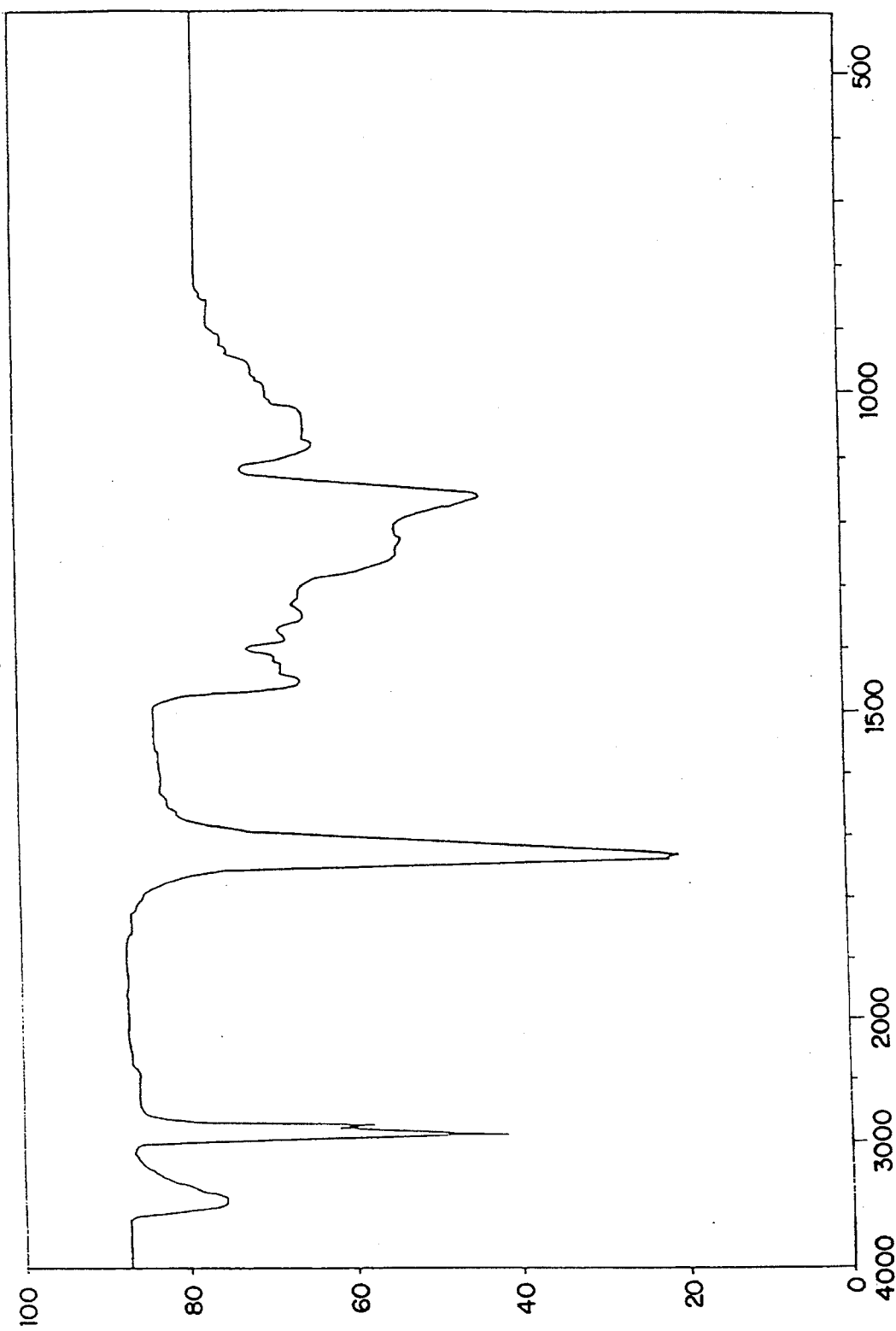
FIG. 5 is an infrared absorption spectral chart for the same.

Further, the NMR spectrum (FIG. 4) and infrared absorption spectrum (FIG. 5) of the product were measured. As a result, these spectra indicated the structure of compounds (I) which had been formed by the ring-opening polymerization of 3 mol, on the average, of ε-caprolactone with the hydroxyl group of compound (II).

Figure 6:
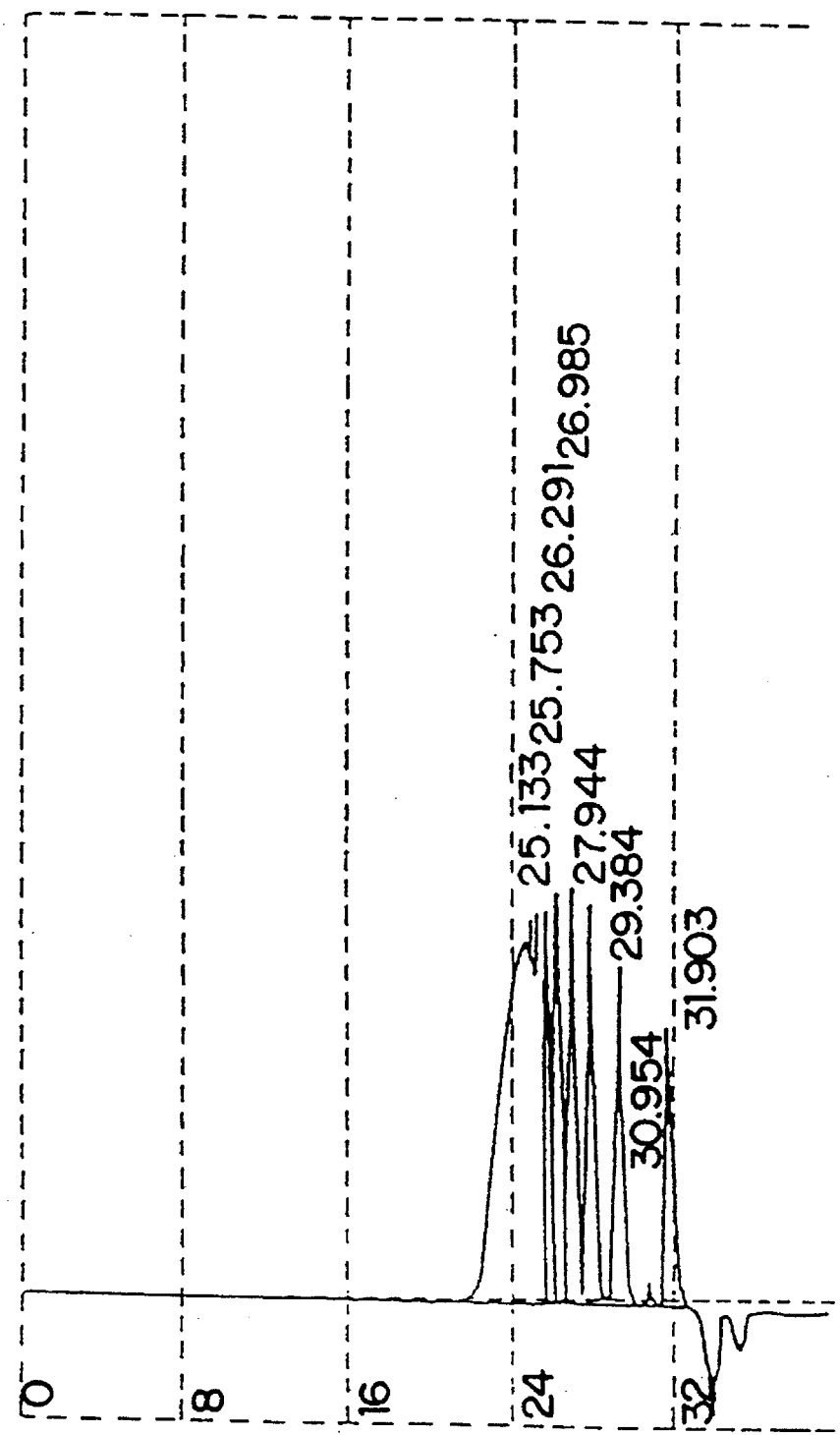
FIG. 6 is a chart obtained in a molecular weight distribution measurement of the same.

Molecular weight distribution was further measured and, as a result, the chart as shown in (FIG. 6) was obtained.

From the ratio between peak areas, this reaction product was found to be a mixture of compounds (I) which had the following distribution in terms of the number of addition-reacted ε-caprolactone introduced in the structural formula of compound (I)

| | |
|---|---|
| y = 0: | 7.71% |
| y = 1: | 8.44% |
| y = 2: | 9.45% |
| y = 3: | 9.79% |
| y = 4: | 9.06% |
| y = 5: | 8.11% |
| y = 6 or more: | 46.96% |

EXAMPLE 3 (Synthesis Route A)

Into the same apparatus as that in Example 1 were introduced 64.0 g of compound ( II ), 171.9 g [3 mol per mol of compound (II)] of ε-caprolactone, and 0.024 g of TBT. Reaction was then conducted at 120° C. for 6 hours, while nitrogen gas was kept being blown in.

The product was analyzed and, as a result, the oxirane oxygen was found to be 2 34%, viscosity 170 cps/45° C., residual ε-caprolactone 0.8%, and acid value 0.9 KOHmg/g.

Figure 7:
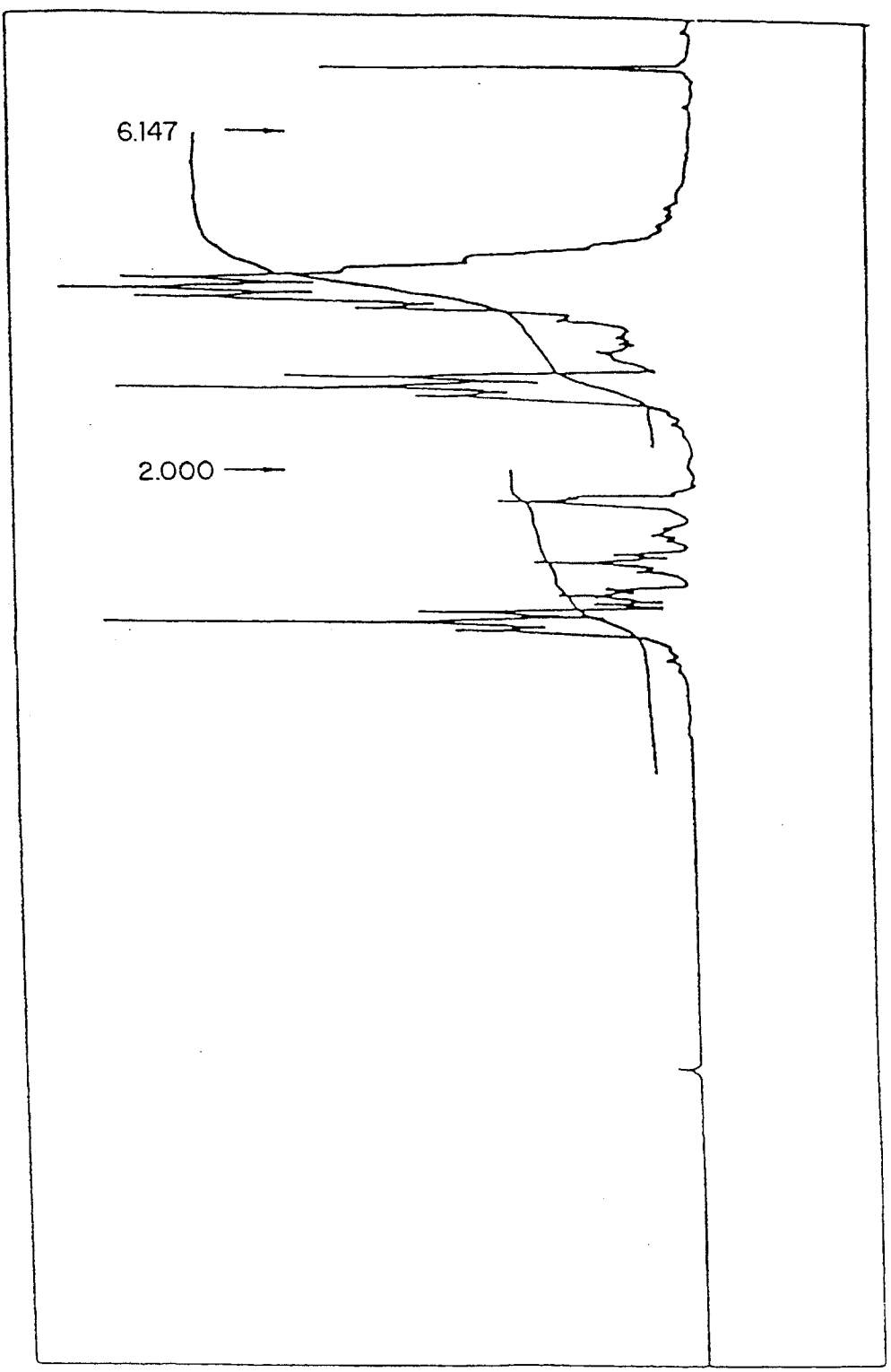
FIG. 7 is an NMR spectral chart for the product obtained in Example 3.
Figure 8:
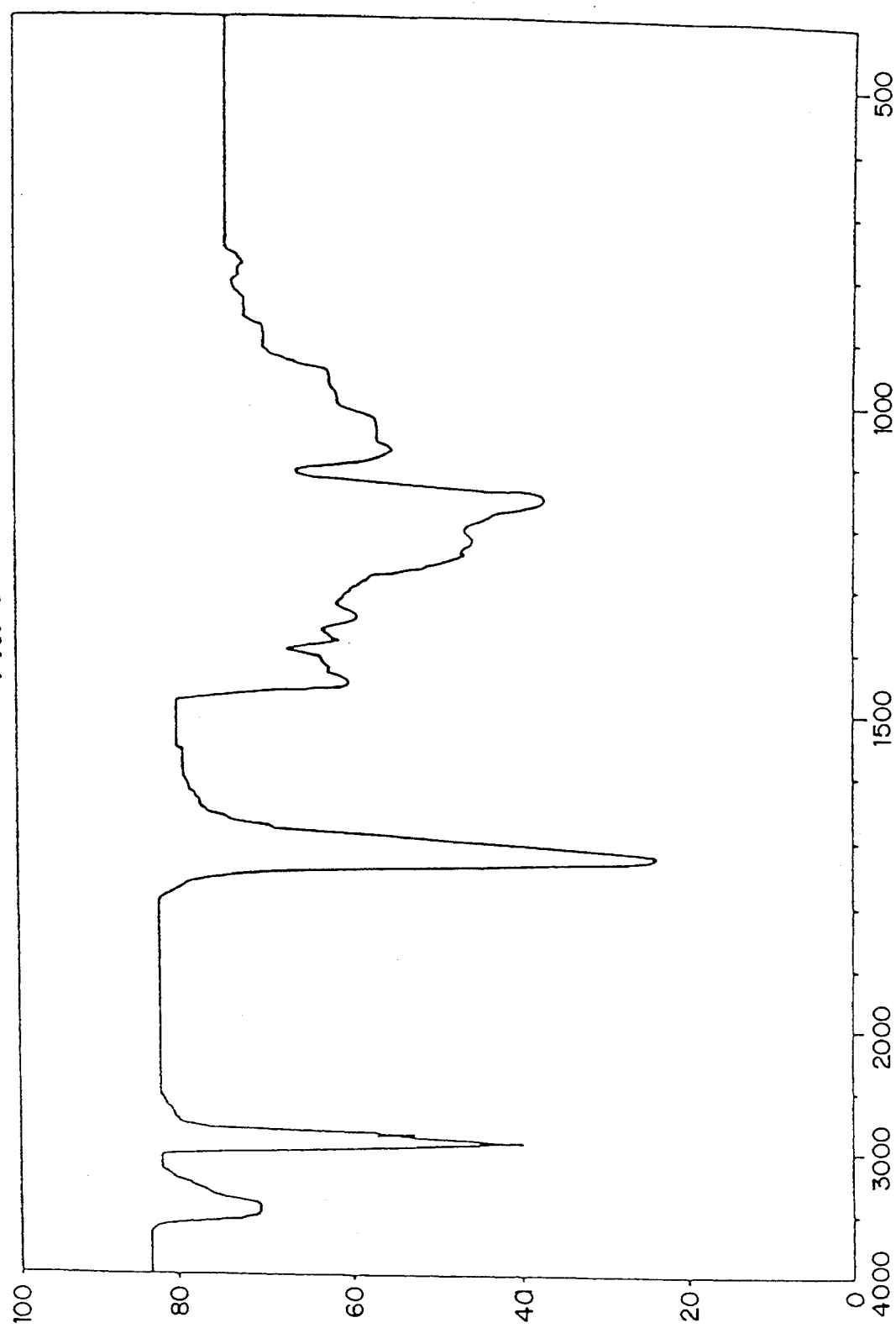
FIG. 8 is an infrared absorption spectral chart for the same.

Further, the NMR spectrum (FIG. 7 ) and infrared absorption spectrum (FIG. 8) of the product were measured. As a result, these spectra indicated the structure of compounds (I) which had been formed by the ring-opening polymerization of ε-caprolactone with the hydroxyl group of compound (II).

Figure 9:
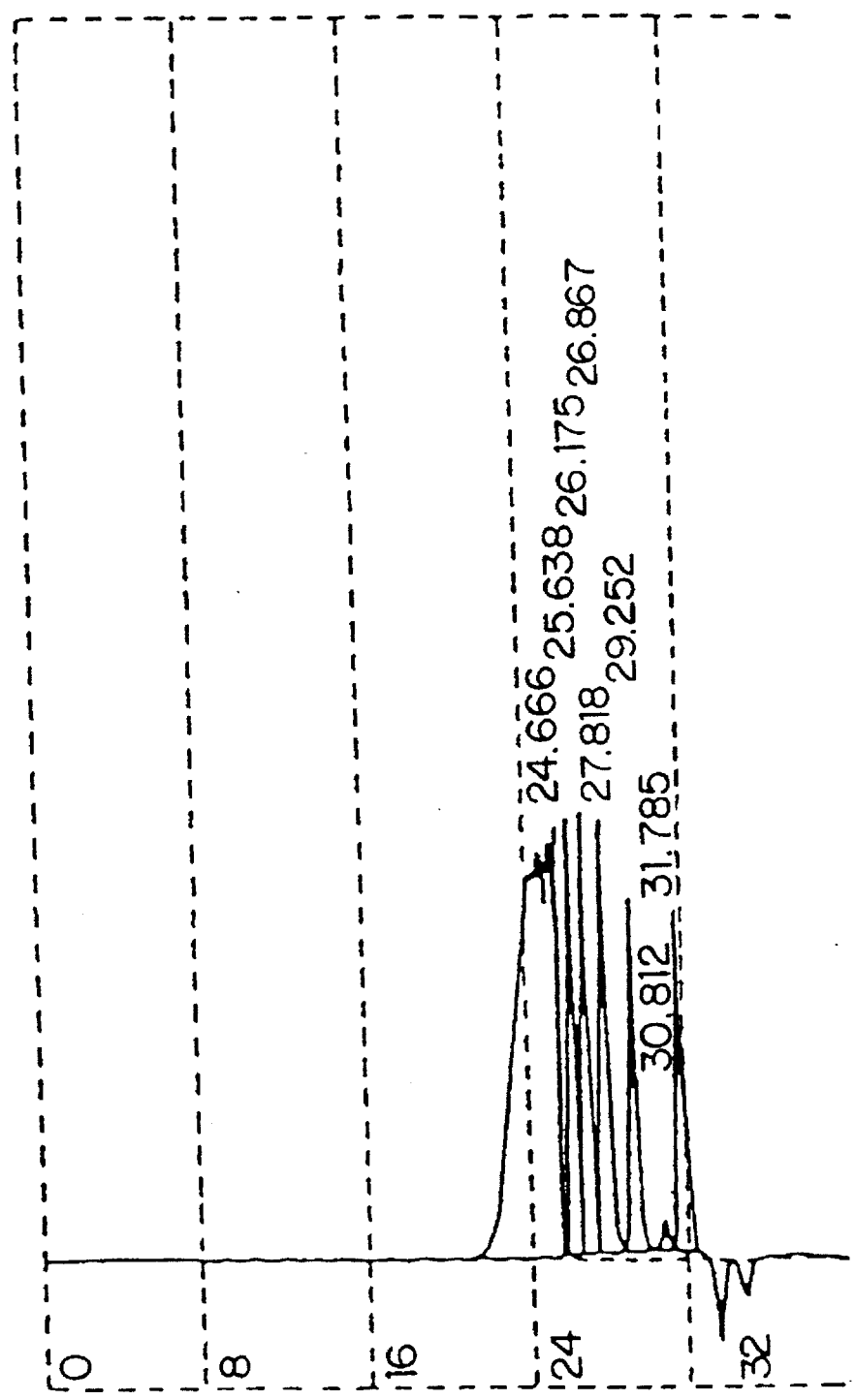
FIG. 9 is a chart obtained in a molecular weight distribution measurement of the same.

Molecular weight distribution was further measured and, as a result, the chart as shown in (FIG. 9) was obtained.

From the ratio between peak areas, this reaction product was found to be a mixture of compounds (I) which had the following distribution in terms of the number of addition-reacted ε-caprolactone introduced in the structural formula of compound (I).

EXAMPLE 4 (Route B)

Into the same apparatus as that in Example 1 were introduced 675.3 g of 3-cyclohexene 1-methanol, 1,374.7 g (2 mol per mol of 3-cyclohexene 1-methanol) of ε-caprolactone, and 0.020 g of TBT. Reaction was then conducted at 170° C. for 3 hours and 30 minutes and, as a result, the residual ε-caprolactone became 0.31% and a composition comprising lactone adducts represented by compounds (III) was obtained. Into a reactor were introduced 1,090 g of this composition comprising lactone adducts represented by compounds (III) and 500 g of ethyl acetate. While the temperature was maintained at 40° C., epoxidization was conducted by reacting the composition with 1.0 g of sodium phosphate as a stabilizer and 1,012 g of a 26.5% ethyl acetate solution of peracetic acid.

After completion of the reaction, the reaction mixture was washed with water and the solvent was removed by distillation, thereby obtaining a composition comprising compounds (I).

This composition was analyzed and, as a result, the oxirane oxygen was found to be 2.78 g, viscosity 172 cps/45° C., iodine value 3.3, and acid value 3.3 KOHmg/g.

Figure 10:
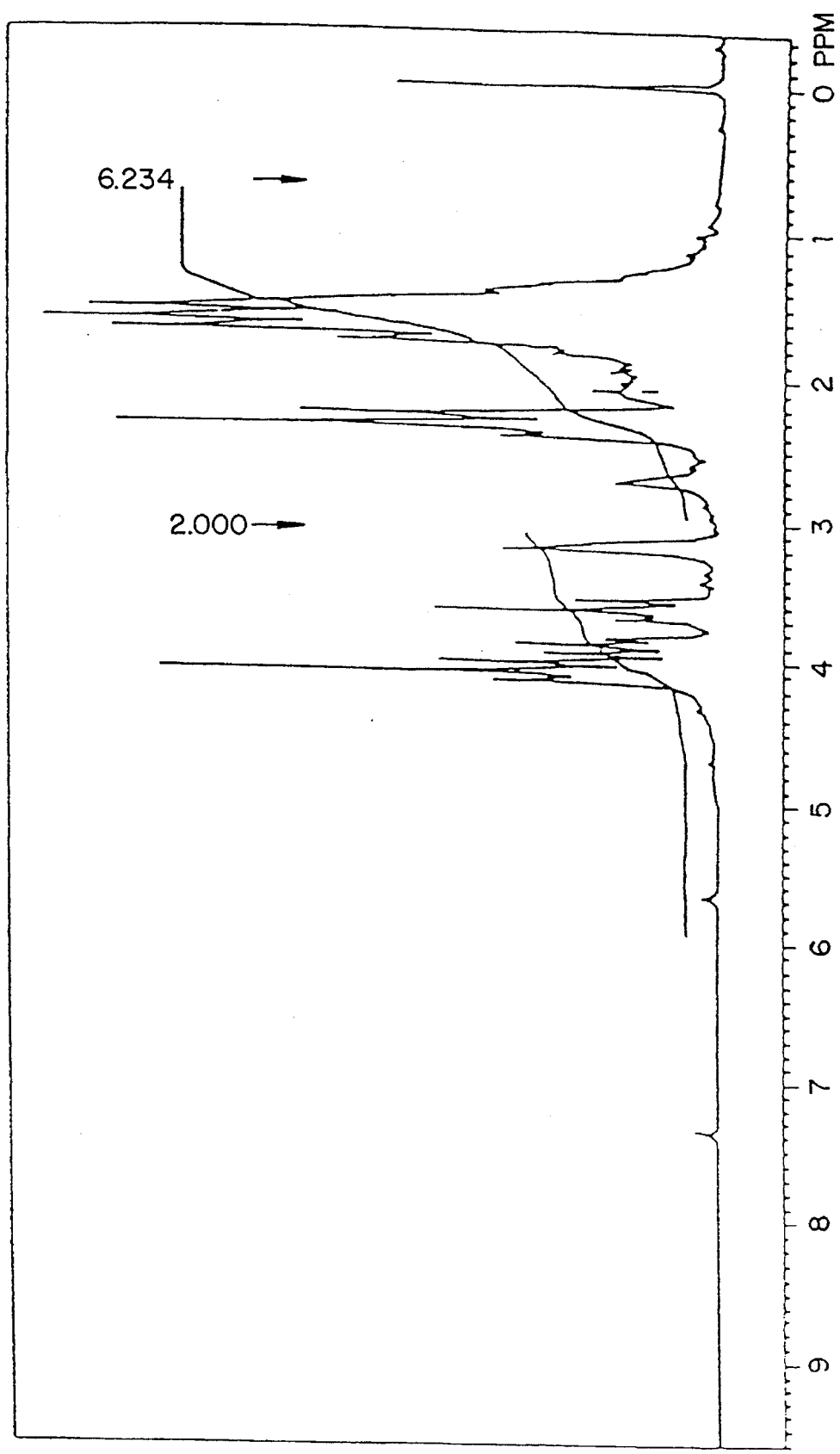
FIG. 10 is an NMR spectral chart for the product obtained in Example 4.
Figure 11:
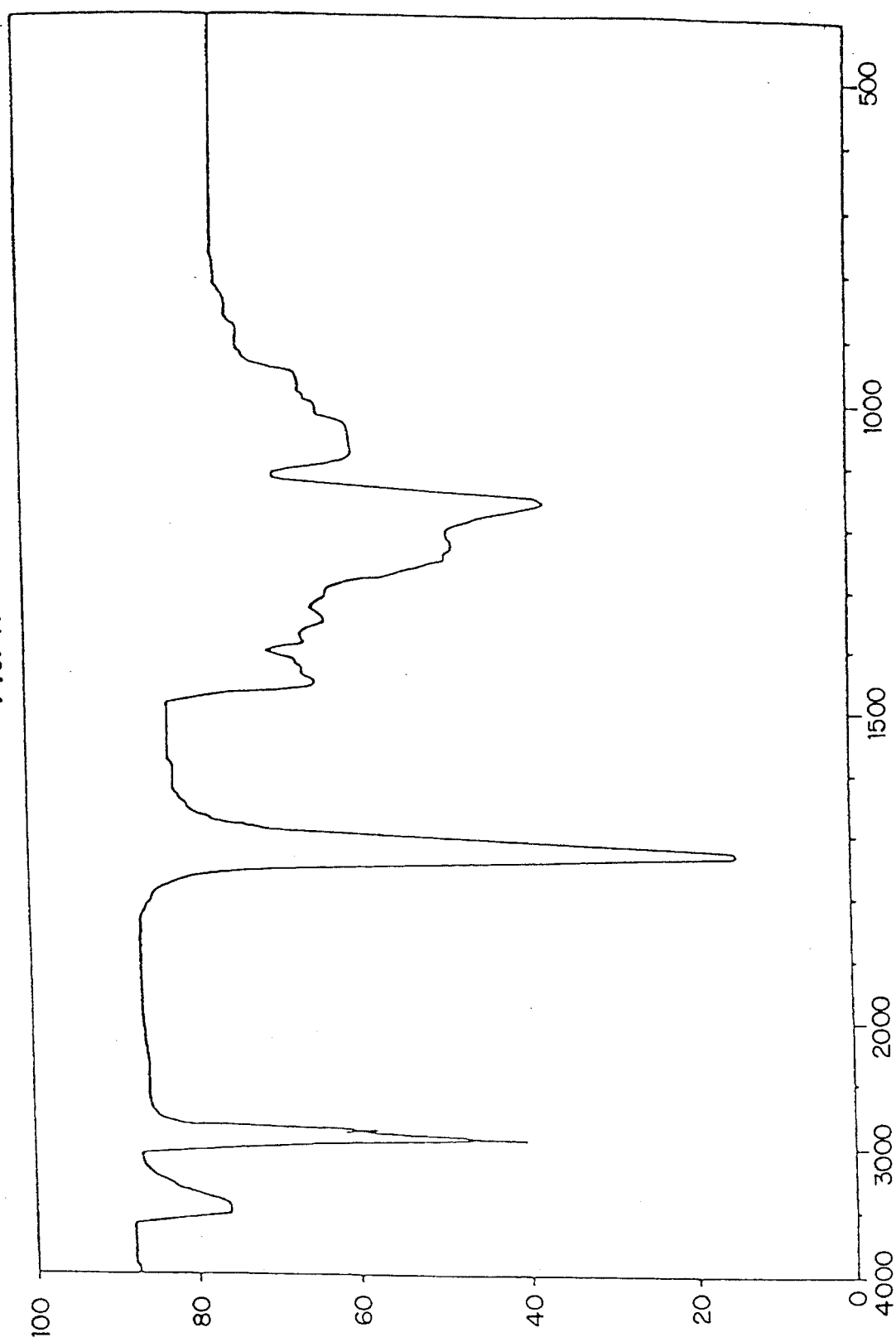
FIG. 11 is an infrared absorption spectral chart for the same.

Further, NMR spectrum (FIG. 10) and infrared absorption spectrum (FIG. 11) were measured and, as a result, the structure of compounds (I) was indicated.

Figure 12:
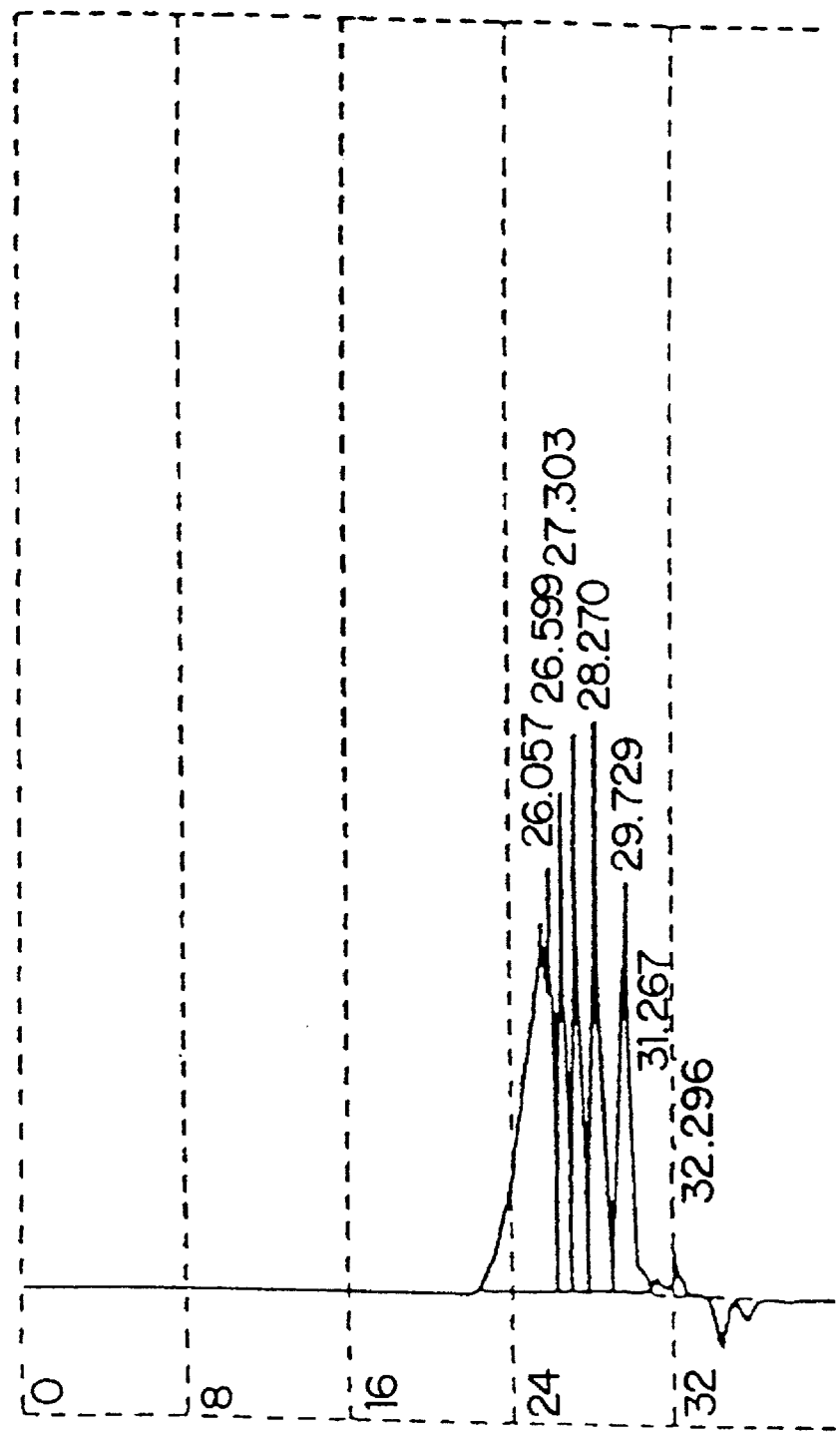
FIG. 12 is a chart obtained in a molecular weight distribution measurement of the same.

Molecular weight distribution was further measured and, as a result, the chart as shown in (FIG. 12) was obtained.

From the ratio between peak areas, this reaction product was found to be a mixture of compounds (I) which had the following distribution in terms of the number of addition-reacted ε-caprolactone introduced in the structural formula of compound (I).

| | |
|---|---|
| y = 0: | 1.04% |
| y = 1: | 12.61% |
| y = 2: | 16.17% |
| y = 3: | 14.96% |
| y = 4: | 13.04% |
| y = 5 or more: | 41.86% |

EXAMPLE 5 (Route B)

Into the same apparatus as that in Example 1 were introduced 259.0 g of 3-cyclohexene 1-methanol, 791.0 g (3 mol per mol of 3-cyclohexene 1-methanol) of ε-caprolactone, and 0.01 g of tetrabutoxytitanium. Reaction was then conducted at 170° C. for 3 hours and 30 minutes and, as a result, the residual ε-caprolactone became 0.62% and a composition comprising lactone adducts represented by compounds (III) was obtained.

Into a reactor were introduced 271 g of this composition comprising lactone adducts represented by compounds (III) and 110.g of ethyl acetate. While the temperature was maintained at 40° C. 0.27 g of sodium phosphate and 161 g of a 29.5% ethyl acetate solution of peracetic acid were added and epoxidization reaction was conducted.

After completion of the reaction, the reaction mixture was washed with water and the solvent was then removed by distillation, thereby obtaining a composition comprising compounds (I).

This composition was analyzed and, as a result, the oxirane oxygen was found to be 2.57%, viscosity 179 cps/45° C., iodine value 2.3, and acid value 2.9 KOHmg/g.

Figure 13:
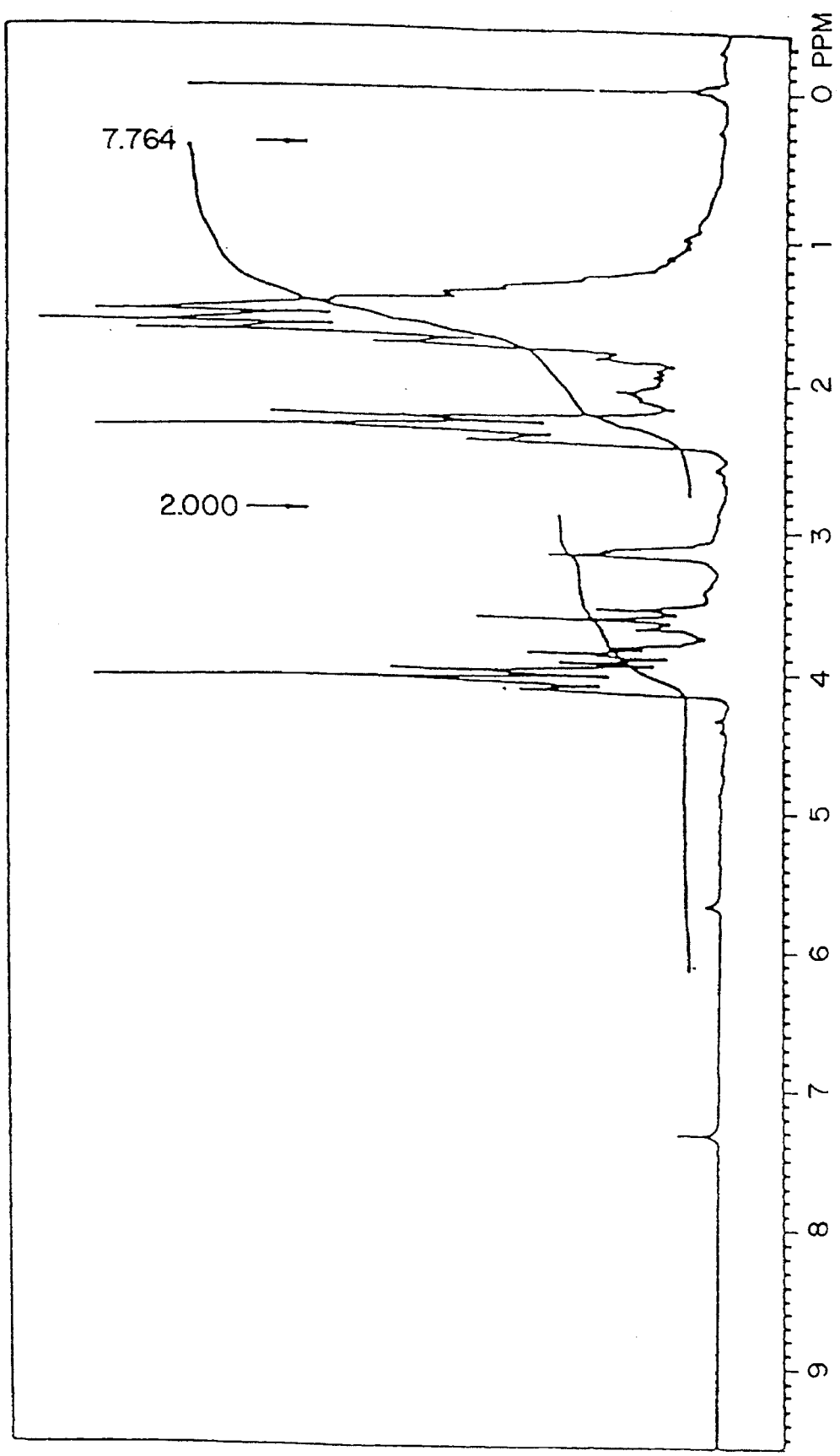
FIG. 13 is an NMR spectral chart for the product obtained in Example 5.
Figure 14:
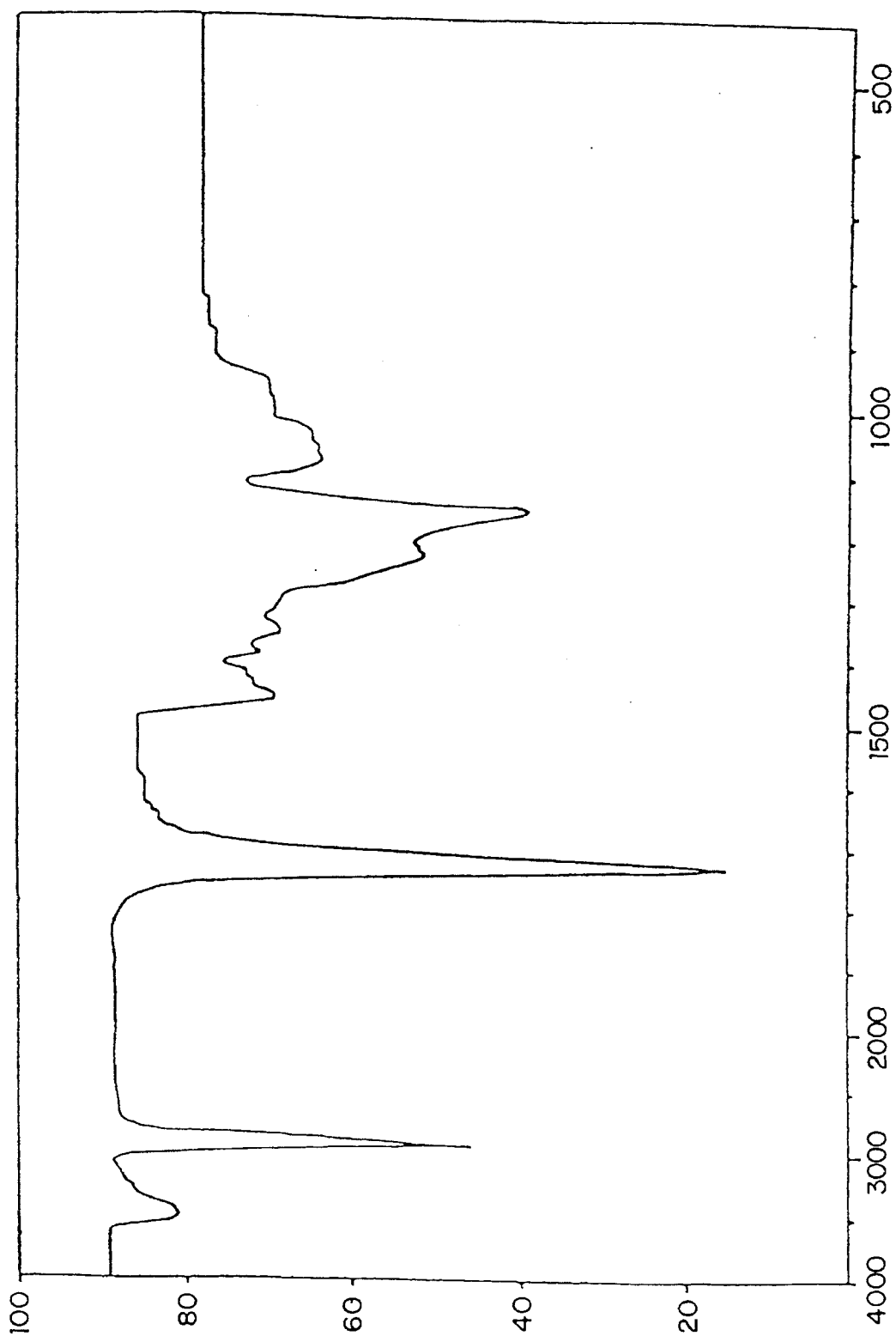
FIG. 14 is an infrared absorption spectral chart for the same.

Both of NMR spectrum (FIG. 13) and infrared absorption spectrum (FIG. 14) indicated the structure of compounds (I).

Figure 15:
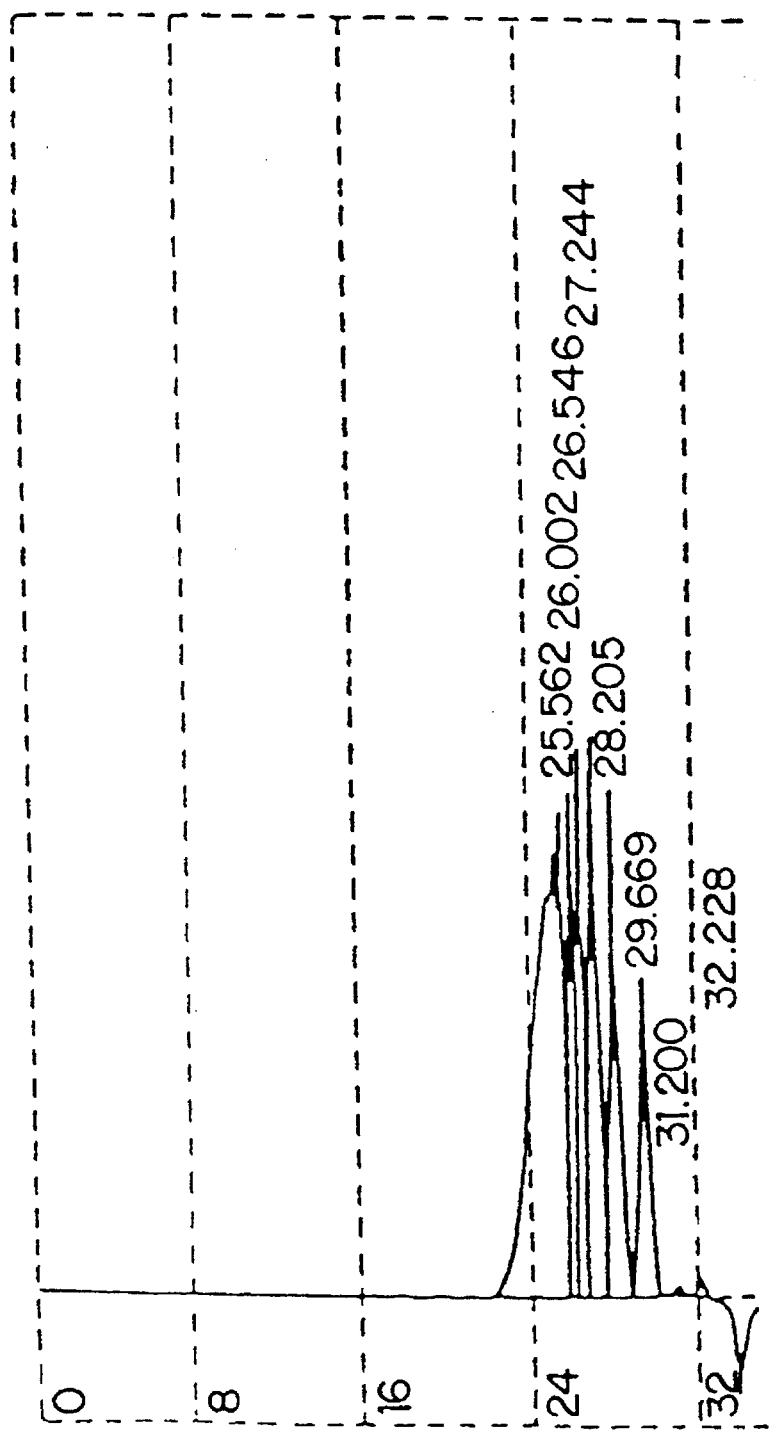
FIG. 15 is a chart obtained in a molecular weight distribution measurement of the same.

Further, from the measurement of molecular weight distribution (FIG. 15), this reaction product was found to be a mixture of compounds (I) which had the following distribution in terms of the number of addition-reacted ε-caprolactone introduced in the structure of compound (I).

| | |
|---|---|
| y = 0: | 0.4% |
| y = 1: | 8.31% |
| y = 2: | 12.0% |
| y = 3: | 12.6% |
| y = 4: | 11.4% |
| y = 5: | 11.1% |
| y = 6 or more: | 43.6% |

EXAMPLE 6 (Route B)

Into the same apparatus as that in Example 1 were introduced 1,061 g of 3-cyclohexene 1-methanol, 1,081 g (1 mol per mol of 3-cyclohexene 1-methanol) of ε-caprolactone, and 0.02 g of tetrabutoxytitanium. Reaction was then conducted at 170° C. for 3 hours and 30 minutes and, as a result, the residual ε-caprolactone became 0.81% and a composition comprising lactone adducts represented by compounds (III) was obtained.

Into a reactor were introduced 800 g of the above composition and 400 g of ethyl acetate. While the temperature was maintained at 40° C. 0.8 g of sodium phosphate as a stabilizer and 984 g of a 26.5% ethyl acetate solution of peracetic acid were added and epoxidization reaction was conducted. The reaction mixture was washed with water and the solvent was then removed by evaporation, thereby obtaining a composition comprising compounds (I).

This composition was analyzed and, as a result, the oxirane oxygen was found to be 3.27%, viscosity 156 cps/45° C., iodine value 2.0, and acid value 3.7 KOHmg/g.

Figure 16:
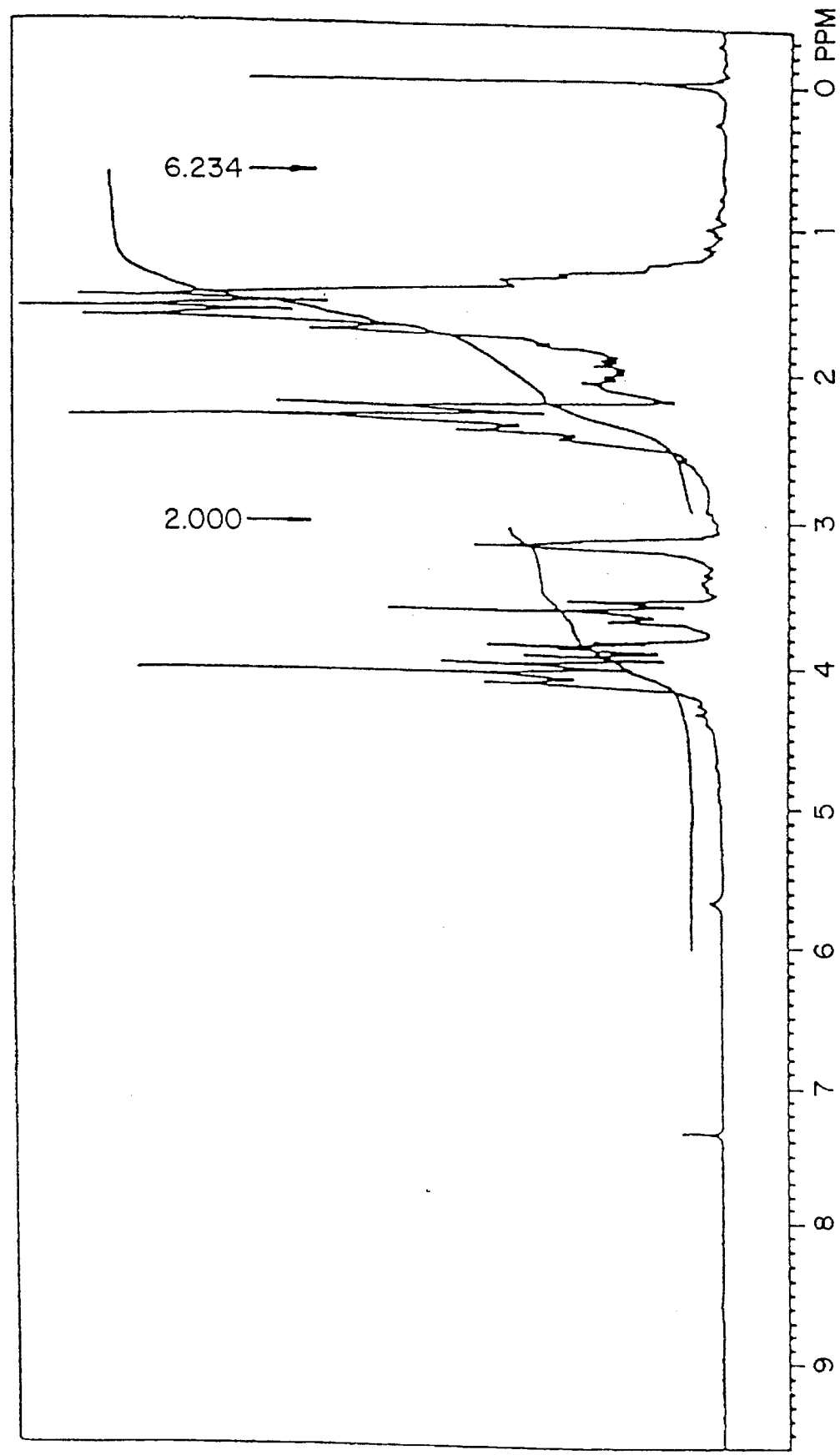
FIG. 16 is an NMR spectral chart for the product obtained in Example 6.
Figure 17:
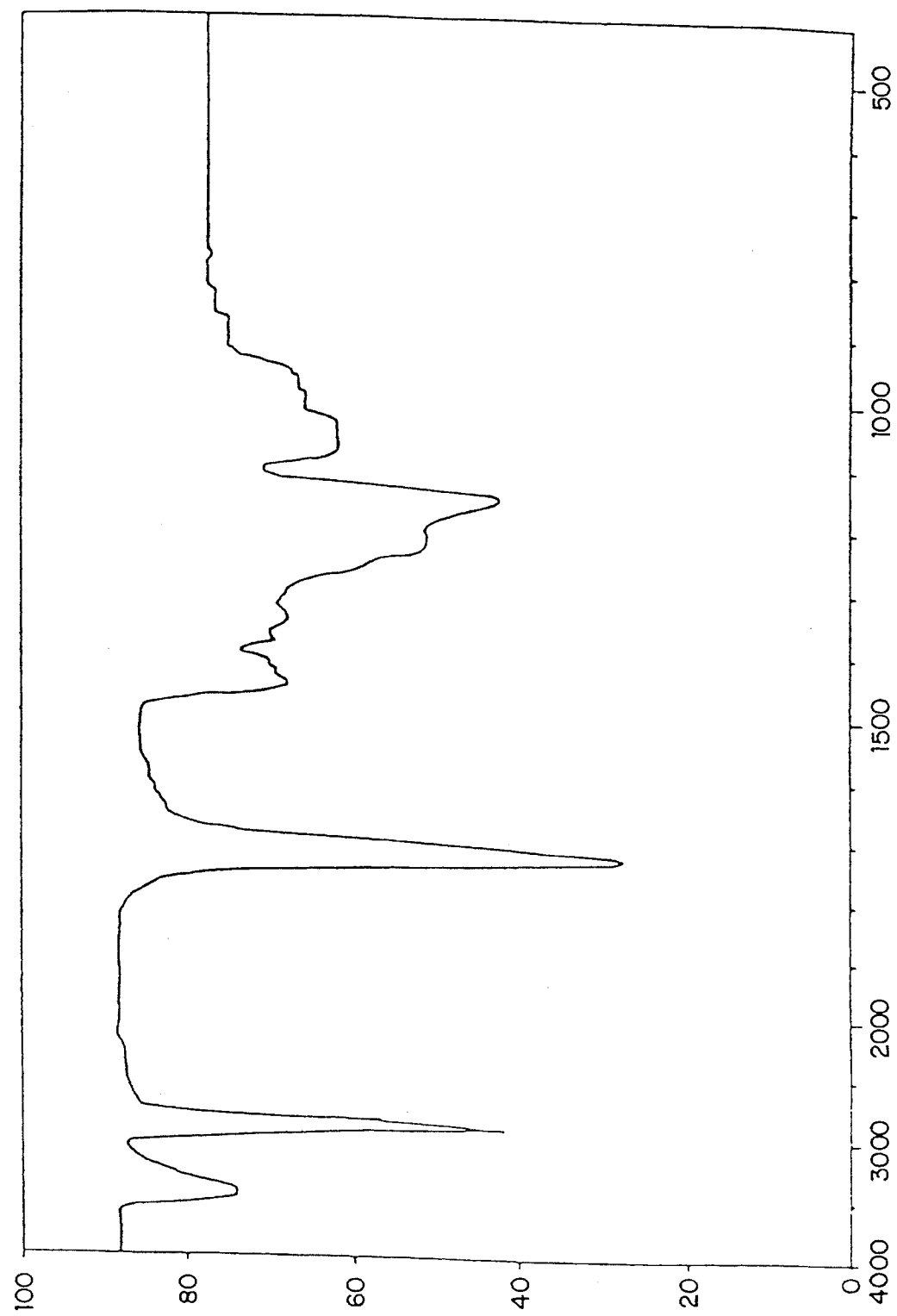
FIG. 17 is an infrared absorption spectral chart for the same.

Both of NMR spectrum (FIG. 16) and infrared absorption spectrum (FIG. 17) indicated the structure of compounds (I).

Figure 18:
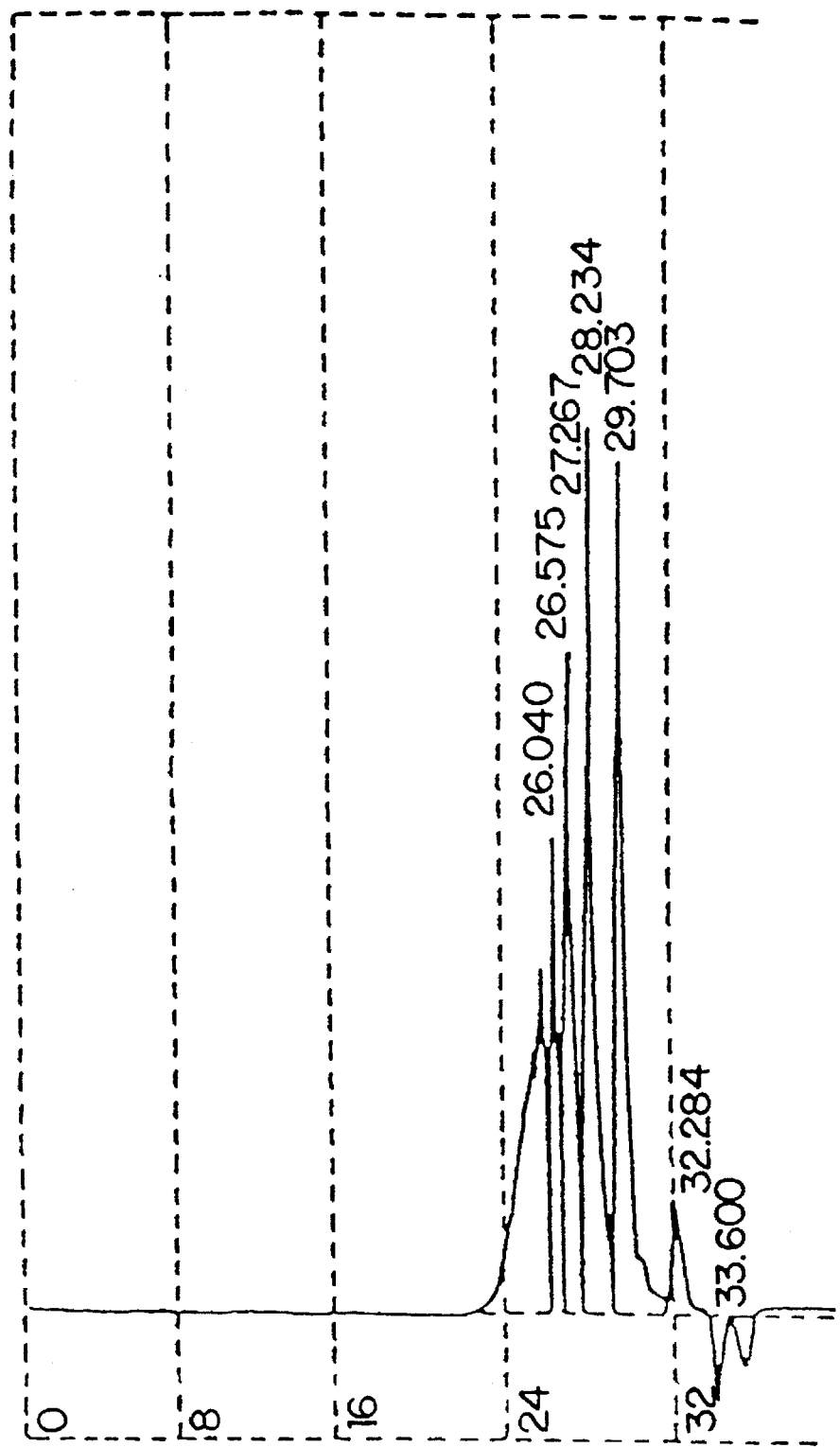
FIG. 18 is a chart obtained in a molecular weight distribution measurement of the same.

Further, from the measurement of molecular weight distribution (FIG. 18), this reaction product was found to be a mixture of compounds (I) which had the following distribution in terms of the number of addition-reacted ε-caprolactone introduced in the structure of compound (I).

| | |
|---|---|
| y = 0: | 3.63% |
| y = 1: | 23.44% |
| y = 2: | 22.42% |
| y = 3: | 16.05% |
| y = 4: | 10.59% |
| y = 5 or more: | 23.59% |

EXAMPLE 7

Into the same apparatus as that in Example 1 were introduced 691.8 g of 3-cyclohexene 1-methanol, 1,408 g (1 mol per mol of 3-cyclohexene 1-methanol) of ε-caprolactone, and 0.04 g of stannous chloride. Reaction was then conducted at 140° C. for 9 hours and, as a result, the residual ε-caprolactone became 0.88% and a composition comprising lactone adducts represented by compounds (III) was obtained.

Into a reactor was introduced 1,321.2 g of the above composition While the temperature was maintained at 40° C. 13 g of sodium phosphate as a stabilizer and 1,109 g of a 29.3% ethyl acetate solution of peracetic acid were added and epoxidization reaction was conducted.

The reaction mixture was washed with water and the solvent was then removed by evaporation, thereby obtaining a composition comprising compounds (I).

This composition was analyzed and, as a result, the oxirane oxygen was found to be 2.64%, viscosity 184 cps/45° C., iodine value 0.9, and acid value 2.9 KOHmg/g.

Figure 19:
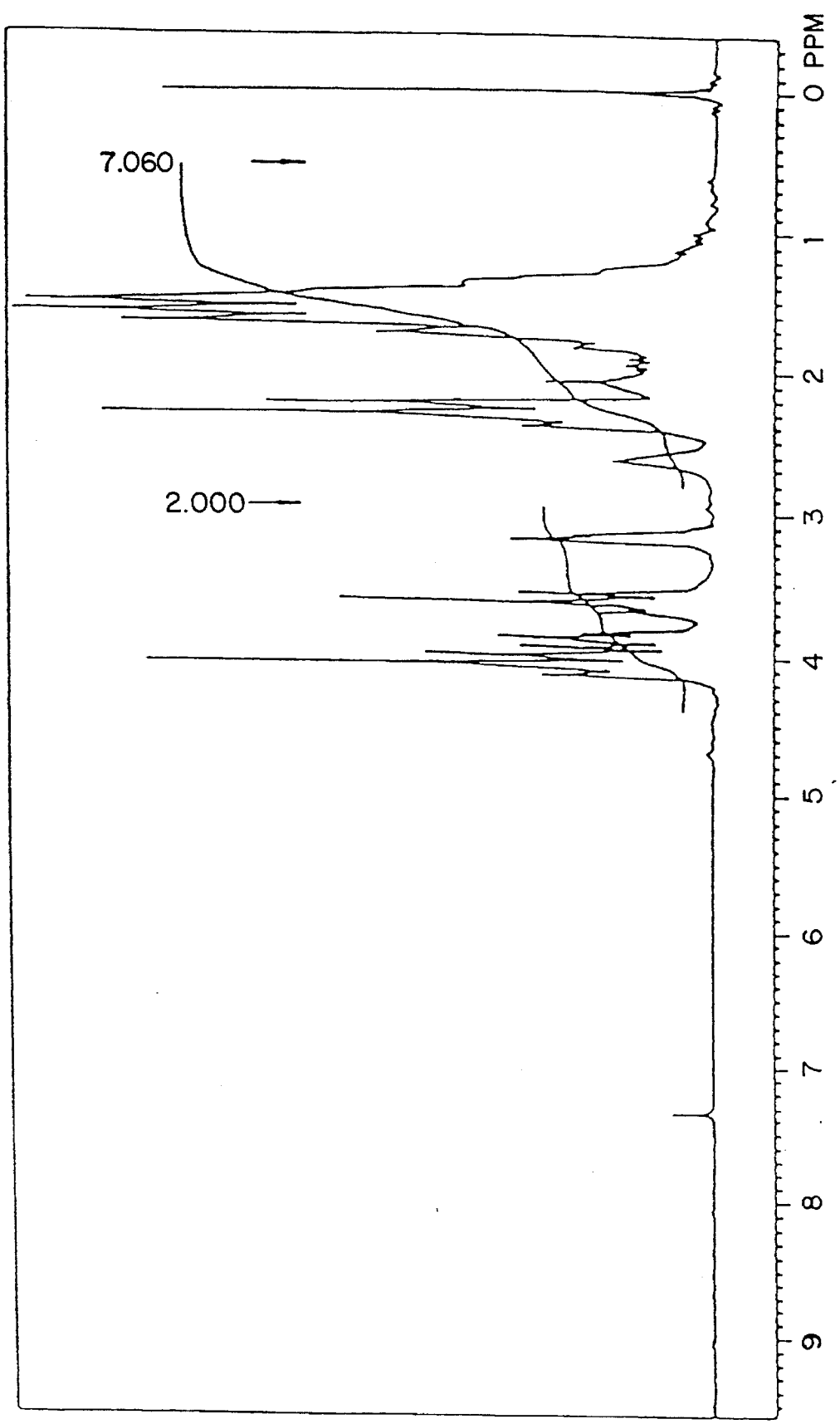
FIG. 19 is an NMR spectral chart for the product obtained in Example 7.
Figure 20:
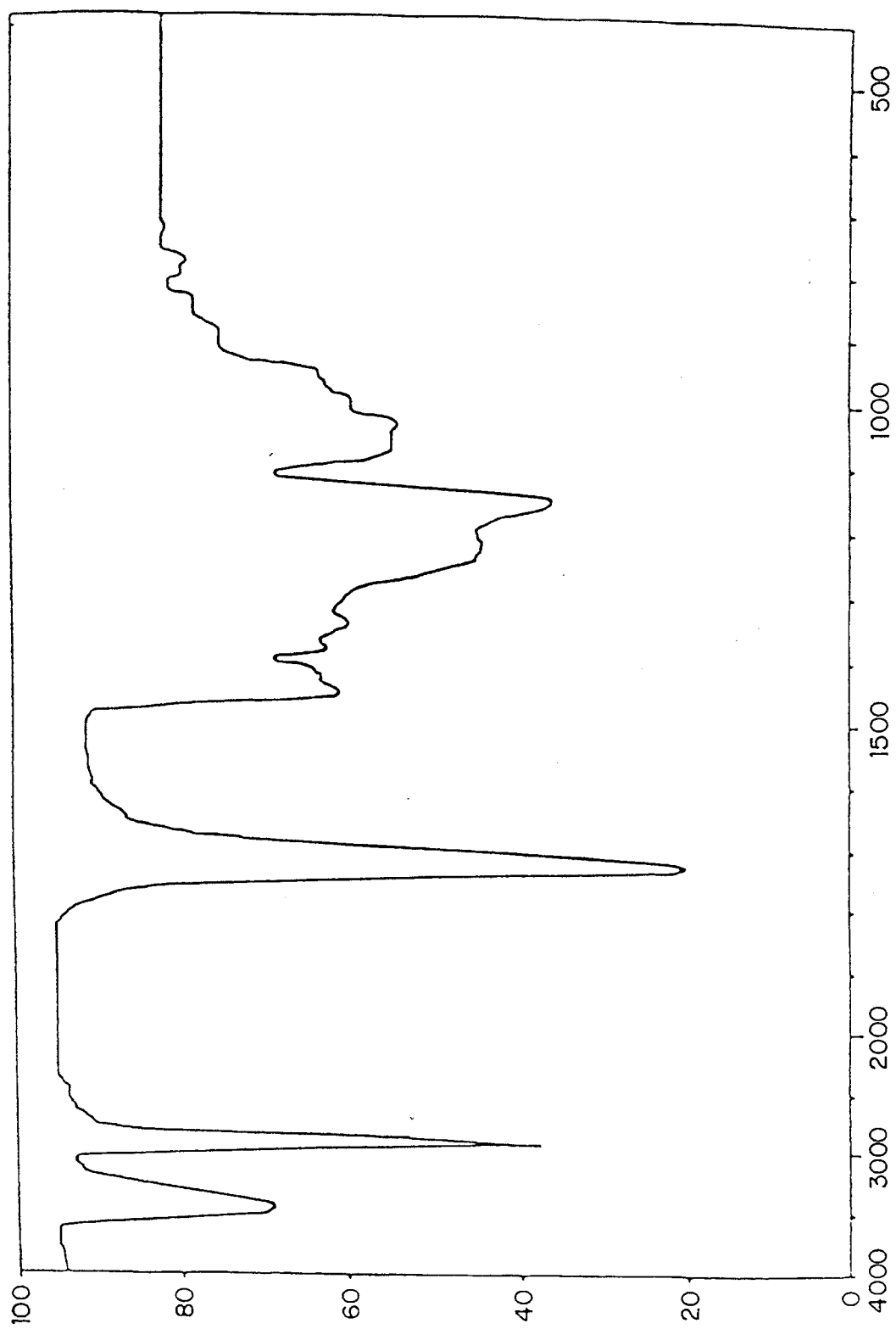
FIG. 20 is an infrared absorption spectral chart for the same.

Further, NMR spectrum (FIG. 19) and infrared absorption spectrum (FIG. 20) indicated that this reaction product had the structure of compounds (I).

Figure 21:
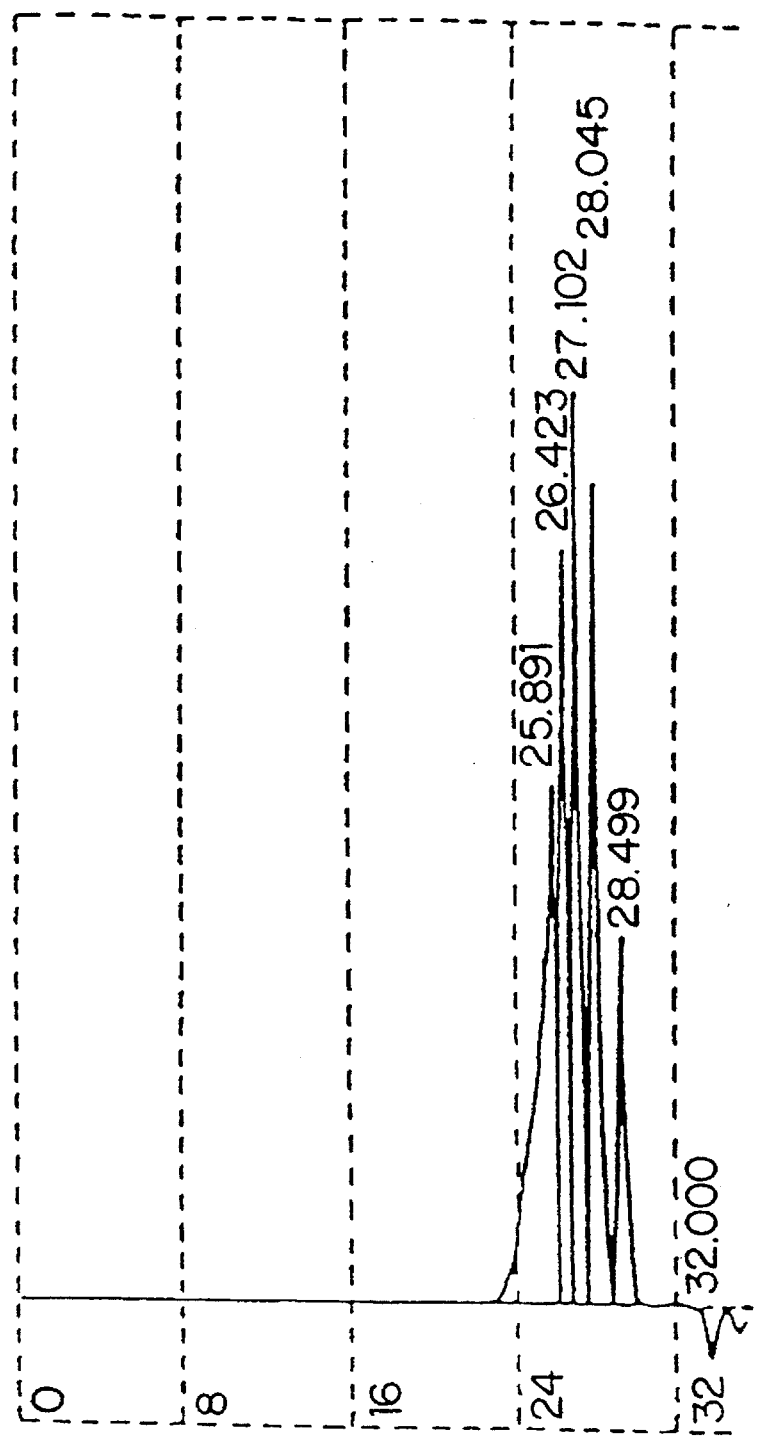
FIG. 21 is a chart obtained in a molecular weight distribution measurement of the same.

Molecular weight distribution was further measured and, as a result, the chart as shown in (FIG. 21) was obtained.

From the areas of peaks, this reaction product was found to be a mixture having the following distribution in terms of the number of addition-reacted ε-caprolactone introduced in the structure of (I).

| | |
|---|---|
| y = 0: | 0.29% |
| y = 1: | 8.82% |
| y = 2: | 19.96% |
| y = 3: | 24.49% |
| y = 4: | 18.49% |
| y = 5 or more: | 27.54% |

EXAMPLE 8

Into the same apparatus as that in Example 1 were introduced 691.8 g of 3-cyclohexene 1-methanol, 1,408 g (1 mol per mol of 3-cyclohexene 1-methanol) of ε-caprolactone, and 0.01 g of stannous chloride. Reaction was then conducted at 150° C. for 6 hours and, as a result, the residual ε-caprolactone became 0.41% and a composition comprising lactone adducts represented by compounds (III) was obtained.

Into a reactor was introduced 1,301 g of the above composition. While the temperature was maintained at 45° C., 29.4 g of sodium phosphate as a stabilizer and 1,061 g of a 29.4% ethyl acetate solution of peracetic acid were added and epoxidization reaction was conducted.

The reaction mixture was treated with a Smith type thin-film evaporator to remove low-boiling ingredients, subsequently diluted with the same amount of ethyl acetate, and neutralized with a two-fold amount of 2.5% NaOH solution.

Thereafter, water-washing was conducted. At the time when the pH had become 6–7, the solvent was removed by distillation, thereby obtaining a composition comprising compounds (I).

This composition was analyzed and, as a result, the oxirane oxygen was found to be 3.45%, viscosity 135 cps/45° C., iodine value 0.9, and acid value 1.0 KOHmg/g.

Figure 22:
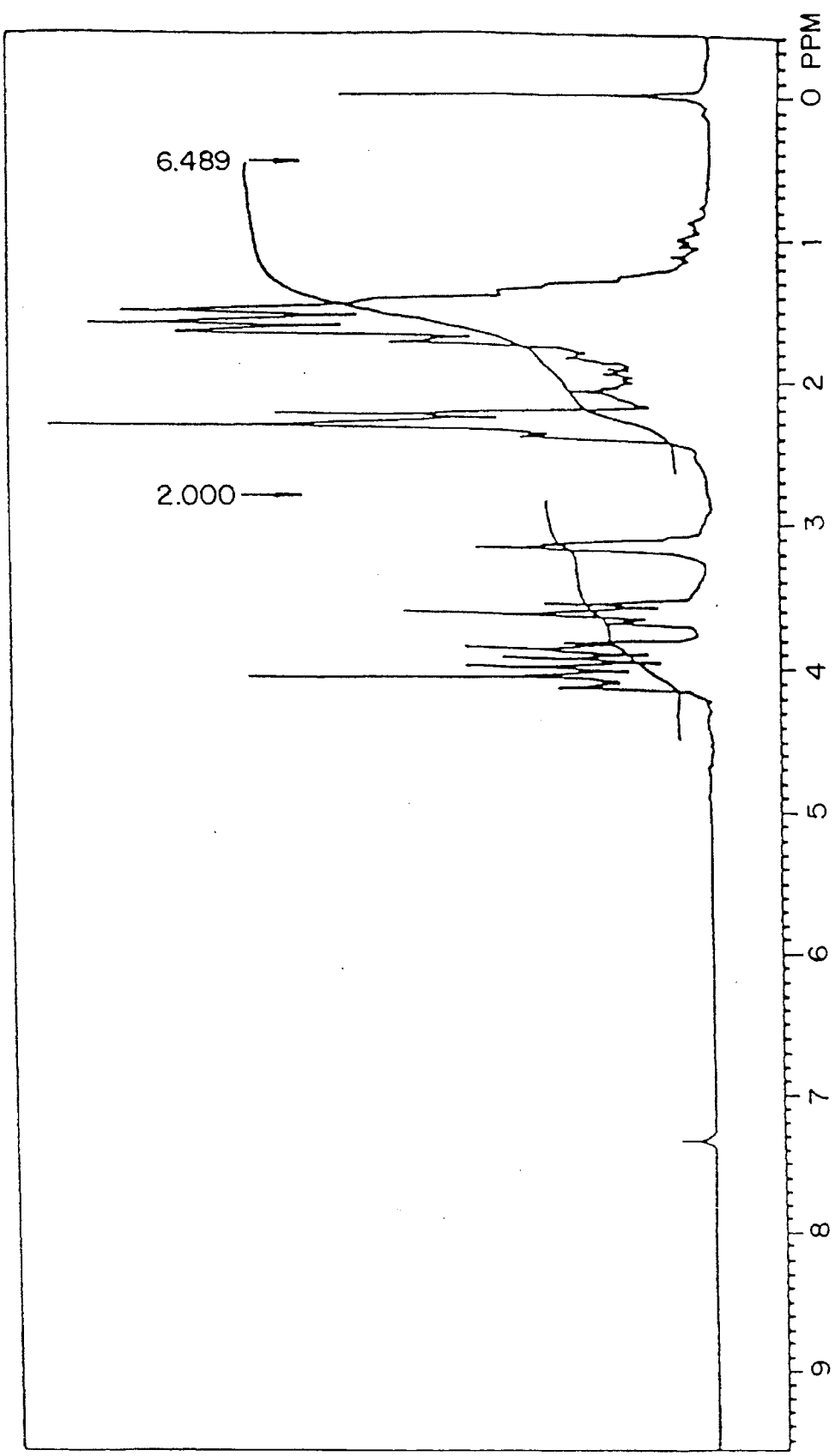
FIG. 22 is an NMR spectral chart for the product obtained in Example 8.
Figure 23:
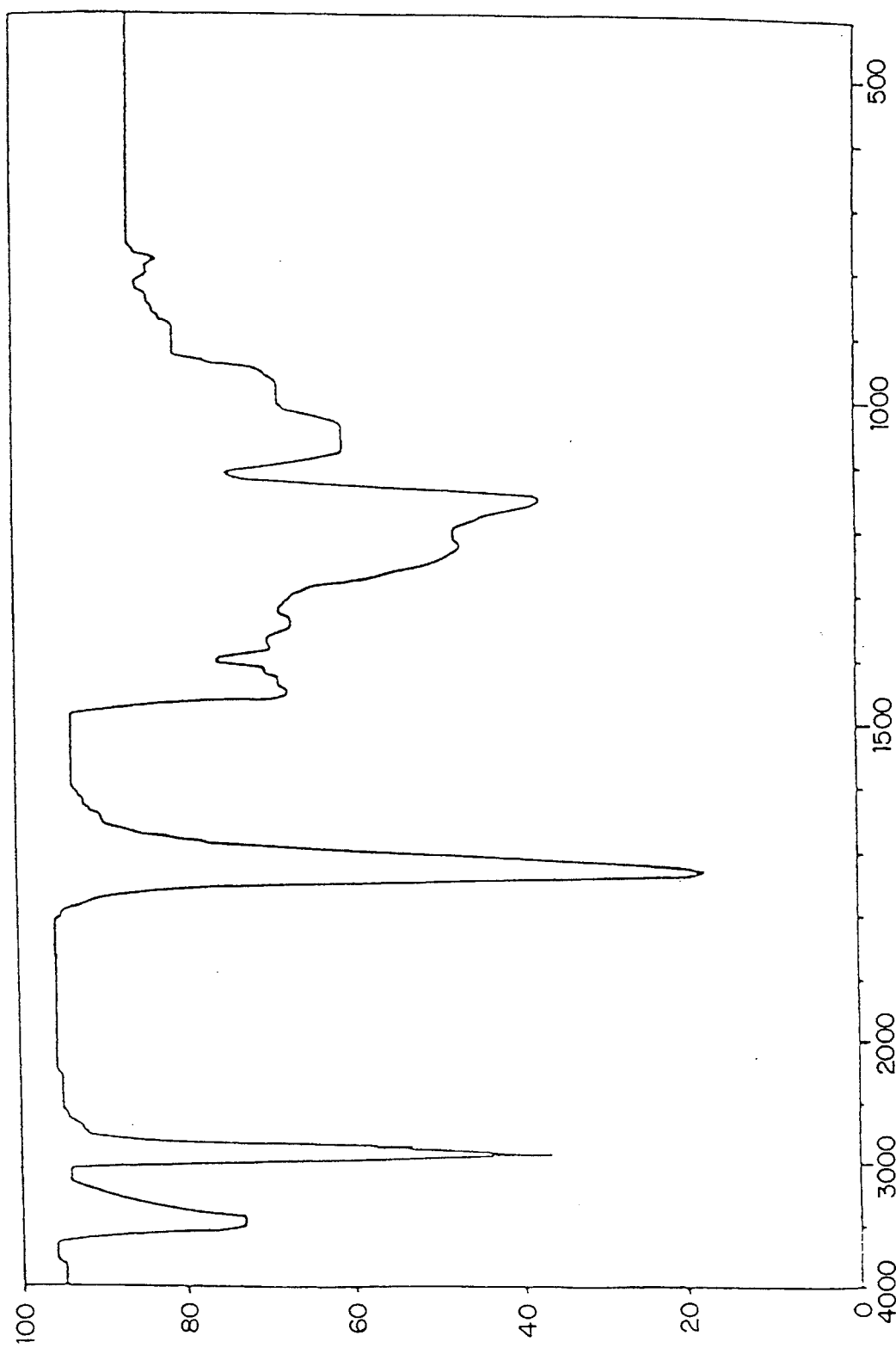
FIG. 23 is an infrared absorption spectral chart for the same.

Further, NMR spectrum (FIG. 22) and infrared absorption spectrum (FIG. 23) indicated that this reaction product had the structure of compounds (I).

Figure 24:
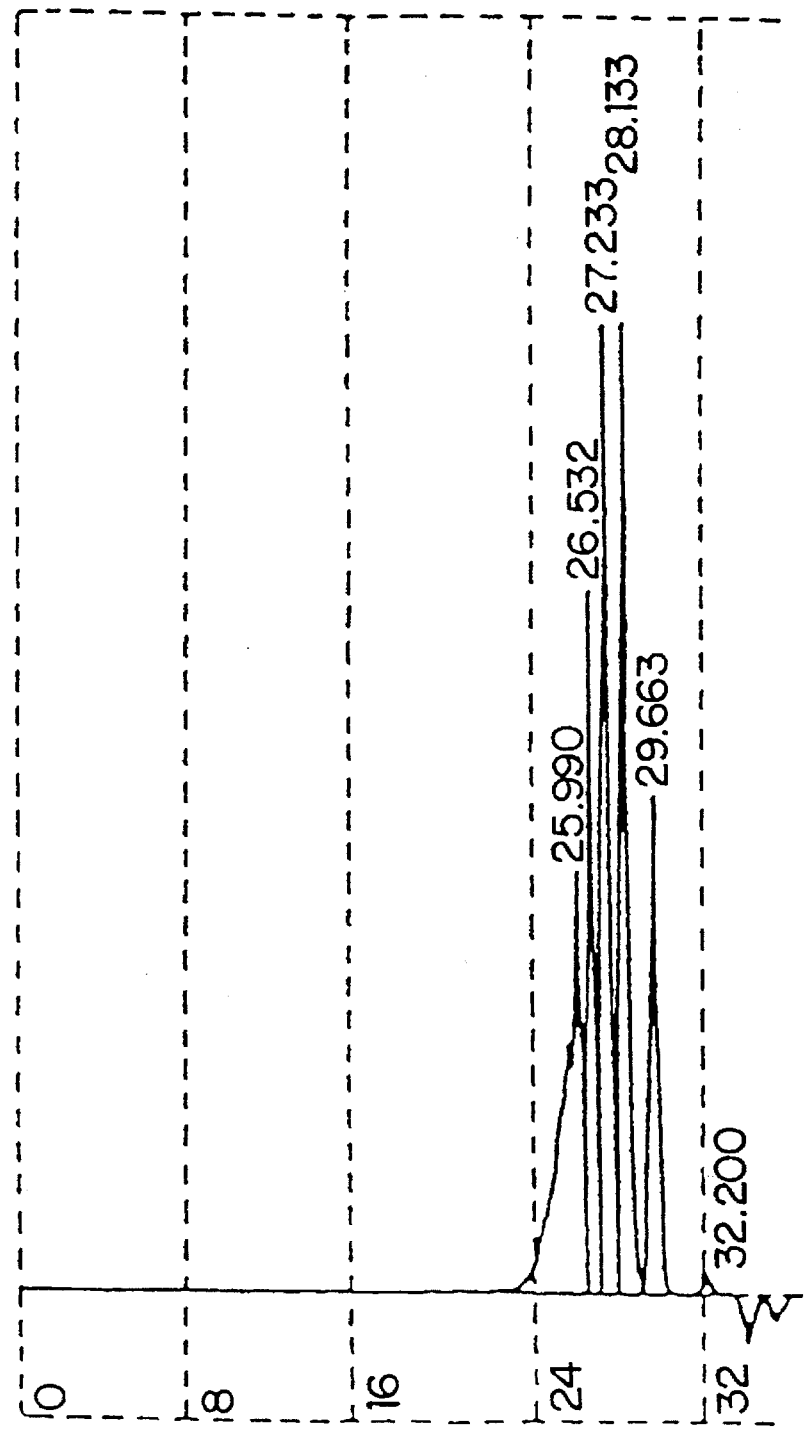
FIG. 24 is a chart obtained in a molecular weight distribution measurement of the same.

Molecular weight distribution was further measured and, as a result, the chart as shown in (FIG. 24) was obtained.

From the areas of peaks, this reaction product was found to be a mixture having the following distribution in terms of the number of addition-reacted ε-caprolactone introduced in the structure of (I).

| | |
|---|---|
| y = 0: | 0.46% |
| y = 1: | 13.11% |
| y = 2: | 24.13% |
| y = 3: | 23.36% |
| y = 4: | 16.69% |
| y = 5 or more: | 22.26% |

POSSIBILITY OF INDUSTRIAL APPLICATION

The composition obtained by the present invention has a highly reactive primary hydroxyl group bonded to a polylactone chain having flexibility and also has an alicyclic epoxy group.

Therefore, a urethane-epoxy resin can be synthesized by reacting the composition with a polyisocyanate compound or a urethane prepolymer.

A blend of this resin with a hardener reactive to epoxy group can be used in various kinds of coating compositions, adhesives, epoxy resins, and the like which are excellent in flexibility, adhesion properties, etc.

Further, since alicyclic epoxy group has enough ability for cationic polymerization, the composition can also be utilized in photocurable coatings, low-temperature-curable coatings, and the like which utilize cationic cure. Furthermore, two processes for efficiently producing the above material have been found, so that it can industrially be produced at low cost.

We claim:

1. A process for producing a composition comprising compounds having the following structural formula (I):

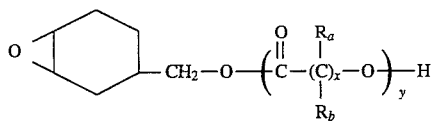
(I)

wherein x represents an integer of 3 to 7, y represents a statistical distribution of integers of 0 to 50, $R_a$ and $R_b$ each independently represents a hydrogen atom, a methyl group or a propyl group, comprising the steps of:

addition-reacting a lactone compound to

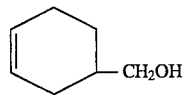

to synthesize a composition comprising compounds having the following structural formula:

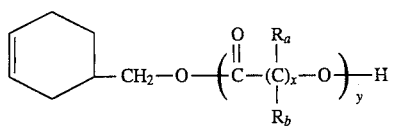
(III)

and;

epoxidizing the composition comprising compounds having structural formula (III) at 0° to 80° C. using a peroxide.

2. The process as claimed in claim 1, wherein the epoxidizing step is conducted in the presence of a phosphorus compound.

3. The process as claimed in claim 2, wherein the epoxidizing step is conducted in the presence of 1 to 1,000 ppm of the phosphorus compound based upon crude reaction liquid.

4. The process as claimed in claim 2, wherein the epoxidizing step is conducted in the presence of a phosphorus compound selected from the group consisting of phosphoric acid, phosphoric acid-potassium, phosphoric acid-sodium, sodium ammonium hydrogenphosphate, pyrophosphoric acid, potassium pyrophosphate, sodium pyrophosphate, potassium 2-ethylhexylpyrophosphate, sodium 2-ethylhexyltripolyphosphate, potassium 2-ethylhexyltripolyphosphate, sodium 2-ethylhexyltetrapolyphosphate and potassium 2-ethylhexyltetrapolyphosphate.

5. The process as claimed in claim 4, wherein the epoxidizing step is conducted in the presence of 1 to 1,000 ppm of the phosphorus compound based upon crude reaction liquid.

6. The process as claimed in claim 1, wherein $R_a$ and $R_b$ each independently represents a hydrogen atom.

* * * * *